United States Patent [19]
Hindsgaul

[11] Patent Number: 6,063,769
[45] Date of Patent: *May 16, 2000

[54] 1-THIOGALACTOSE DERIVATIVES

[75] Inventor: Ole Hindsgaul, Edmonton, Canada

[73] Assignee: Synsorb Biotech, Inc., Calgary, Canada

[*] Notice: This patent is subject to a terminal disclaimer.

[21] Appl. No.: 08/751,510

[22] Filed: Nov. 15, 1996

Related U.S. Application Data

[60] Provisional application No. 60/030,794, Nov. 14, 1996.

[51] Int. Cl.$^7$ .............................. A61K 31/70; C07H 15/24

[52] U.S. Cl. .......................... 514/24; 536/4.1; 536/17.2; 536/17.5; 536/17.6; 536/17.9

[58] Field of Search ..................... 536/4.1, 17.2, 536/17.5, 17.6, 17.9; 514/24

[56] References Cited

U.S. PATENT DOCUMENTS

| | | | |
|---|---|---|---|
| 4,137,401 | 1/1979 | Lemieux et al. | |
| 5,580,858 | 12/1996 | Ippolito et al. | |
| 5,780,603 | 7/1998 | Hindsgaul | 536/4.1 |

FOREIGN PATENT DOCUMENTS

| | | |
|---|---|---|
| 0 649 021 A1 | 4/1995 | European Pat. Off. |
| WO 94/19360 | 9/1994 | WIPO . |
| WO 95/21628 | 8/1995 | WIPO . |

OTHER PUBLICATIONS

Spangler, B. D., "Structure and Function of Cholera Toxin and Related *Escherichia coli* Heat–Labile Enterotoxin", *Microbiological Reviews*, 56(4):622–647 (1992).

Hol, W., et al., "Structure and Function of *E. coli* Heat–Labile Enterotoxin and Cholera Toxin B Pentamer", *Bacterial Toxins and Virulence Factors in Disease*, Ed. by J. Moss et al., Marcel Dekker, Inc. (1995).

Evans et al., "The Asymmetric Synthesis of α–Amino Acids. Electrophilic Azidation of Chiral Imide Enolates, a Practical Approach to the Synthesis of (R)–and (S)–α–Azido Carboxylic Acids", *J. Amer. Chem. Soc.*, 112:4011–4030 (1990).

Williams, R. et al., "Asymmetric Synthesis of Monosubstituted and α,α–Disubstituted α–Amino Acids via Diastereoselective Glycine Enolate Alkylations", *J. Amer. Chem. Soc.*, 113:9276–9286 (1991).

Svennerholm, A–M. et al., Identification of *Escherichia coli* Heat–Labile Enterotoxin by Means of a Ganglioside Immunosorbent Assay ($G_{m1}$–ELISA) Procedure, *Current Microbiology*, 1:19–23 (1978).

Pu et al., *J. Org. Chem.*, 56:1280–1283 (1991).

Kagen et al., *Synlett*, 1990, 643–650.

E. Hasegawa, K. Ishiyama, T. Horaguchi, T. Shimizu, *J. Org. Chem.*, 1991, 56, 1631–1635.

H. Paulsen, K.Eberstein, W. Koebernick, *Tetrahedron Letters*, 1974, 4377–4380.

M. Dubois et al., *Anal. Chem.*, 28, (1979) 350–356.

T. Mukaiyama et al., *Tetrahedron Letters*, 56, 5907–5908 (1968).

H. H. Westal et al., "Methods of Enzymology,"34(b), 64 (1974).

A. Hasagawa et al., *J. Carbohydrate Chem.*, 5, 11–19 (1986).

D.W.K. Acheson et al., *Infect. Immun.*, 61 (3), 1098–1104 (1993).

A. Ramesh et al., *J. Biotechol.*, 43 (1), 45–51–(1995).

P. Fugedi et al., *Glycoconjugate Journal*, 4, 97–100 (1987).

E. Bar–Guilloux et al., *Carbohydrate Research*, 250 (1), 1–8 (1993).

M. Cerny et al., *Collection of Czechoslovak Chemical Communications*, 61 (10), 1489–1500 (1996).

G. Vic et al., *Tetrahedron: Asymmetry*, 5 (12), 2513–1516 (1994).

J. DeFaye et al., *Carbohydrate Research*, 253, 185–194 (1994).

I. Tvaroska et al., *Carbohydrate Research*, 229 (2), 225–231 (1992).

M.–O. Contour–Galcera et al., *Carbohydrate Research*, 281 (1), 99–118 (1996).

M. Petrusova et al., *Carbohydrate Research*, 283, 73–80 (1996).

Witczak, Z.J. et al., Synthesis of L–Fucopyranosyl, 4–Thiodisacchasrides from Levoglucosenone and Their Inhibitory Activity on α–L–Fucosidase, "Bioorganic & Medicinal Chemistry Letters", vol. 5, No. 18:2169–2174, 1995.

J. Defaye, et al., "Thiooligosaccharides: Their Synthesis and Reactions with Enzymes" in *Studies in Natural Products Chemistry*, vol. 8, pp. 315–357, Elsevier Sciences Publishers (1991).

Collins et al., "Monosaccharides: Their Chemistry and Their Roles in Natural Products," John Wiley & Sons, Chichester, England, 1995, pp. 97–106.

Ferrier et al., *Carbohydrate Chemistry* 1996, 28, 158–164.

Ferrier et al., *Carbohydrate Chemistry* 1993, 27, 140–147.

Williams et al., *Carbohydrate Chemistry* 1983, 17, 116–119.

Horton et al., Thio Sugars and Derivatives, In "The Carbohydrates: Chemistry and Biochemistry", $2^{nd}$ Edition, Pigman et al., eds. Academic Press, New York, 1980.

Schnabeirauch et al, *Helv. Chim. Acta* 1994, 77, 778.

*Primary Examiner*—Elli Peselev
*Attorney, Agent, or Firm*—Burns, Doane, Swecker & Mathis, LLP

[57] ABSTRACT

Disclosed are novel 1-thiogalactose derivatives which inhibit binding of heat labile toxin (LT) and/or chlorea toxin (CT) to cell surface receptors either in vitro or in vivo. Additionally, disclosed are compounds which inhibit binding of enterovirulent microorganisms (e.g., bacteria, virus, fungi, and the like) such as *Vibrio cholerae* and enterotoxigenic strains of *Escherichia coli* to cell surface receptors.

13 Claims, 2 Drawing Sheets

6,063,769

1-THIOGALACTOSE DERIVATIVES

REFERENCE TO PROVISIONAL APPLICATION

This application claims the benefit of Provisional Application Ser. No. 60/030,794 filed on Nov. 14, 1996 as Attorney Docket No. 026579-064 and entitled "1-Thiogalactose Derivatives".

BACKGROUND OF THE INVENTION

1. Field of the Invention

This invention relates to novel 1-thiogalactose derivatives which inhibit binding of heat labile toxin (LT) and/or chlorea toxin (CT) to cell surface receptors either in vitro or in vivo. Additionally, the compounds of this invention inhibit binding of enterovirulent microorganisms (e.g., bacteria, virus, fungi, and the like) such as *Vibrio cholerae* and enterotoxigenic strains of *Escherichia coli* to cell surface receptors.

2. References

The following publications, patents and patent applications are cited in this application as superscript numbers:

[1] Spangler, B. D., "Structure and Function of Cholera Toxin and Related *Escherichia coli* Heat-Labile Enterotoxin", *Microbiological Reviews*, 56(4):622–647 (1992).

[2] Hol, W. G. J., et al., "Structure and Function of *E. coli* Heat-Labile Enterotoxin and Cholera Toxin B Pentamer", *Bacterial Toxins and Virulence Factors in Disease*, Ed. by J. Moss et al., Marcel Dekker, Inc. (1995).

[3] Williams (ed.), *Synthesis of Optically Active α-Amino Acids*, Pergamon Press (1989).

[4] Evans et al., *J. Amer. Chem. Soc.*, 112:4011–4030 (1990).

[5] Pu et al., *J. Amer. Chem. Soc.*, 56:1280–1283 (1991).

[6] Williams et al., *J. Amer. Chem. Soc.*, 113:9276–9286 (1991).

[7] Svennerholm, A-M. et al., *Current Microbiology*, 1:19–23 (1978).

All of the above publications, patents and patent applications are herein incorporated by reference in their entirety to the same extent as if each individual publication, patent or patent application was specifically and individually indicated to be incorporated by reference in its entirety.

3. State of the Art

Toxins produced by bacteria and other organisms are known to cause a number of human diseases, including many diarrheal diseases. For example, heat-labile enterotoxin ("LT"), secreted by certain enterotoxigenic strains of *Escherichia coli,* has been identified as one of the causative agents of bacterial-induced traveller's diarrhea.[1] Additionally, cholera toxin ("CT"), produced by *Vibrio cholerae,* has been identified as the causative agent of the severe diarrheal disease, cholera.[1]

Heat-labile enterotoxin and cholera toxin are known to bind to oligosaccharide receptors on host cells as an initial step in the pathological development of the associated disease condition.[2] Specifically, both LT and CT are known to bind to ganglioside $G_{M1}$, a glycosphingolipid situated in the outer leaflet of the host cell membrane.[2] $G_{M1}$ has a characteristic pentasaccharide structure, i.e., Gal(β1→3)GalNAc(β1→4){NeuAc(α2→3)}Gal(β1→4)Glc, on its surface which serves as a receptor for LT and CT. LT is also known to bind to other gangliosides, such as ganglioside $G_{D1b}$.

Additionally, enterovirulent microorganisms (e.g., bacteria, virus, fungi, and the like) such as *Vibrio cholerae* and enterotoxigenic strains of *Escherichia coli* can directly bind to cell surface receptors forming a colony at the point of attachment. Such binding is detrimental because it permits expressed toxin to immediately interact with the cell surface.

In order to treat or prevent bacterial-induced traveller's diarrhea and/or cholera, it would be highly desirable to be able to inhibit the binding of LT and/or CT to their corresponding cell surface receptors as well as the binding of *Vibrio cholerae* and enterotoxigenic strains of *Escherichia coli* can directly bind to cell surface receptors. The present invention provides novel 1-thiogalactose derivatives which effectively inhibit such binding.

SUMMARY OF THE INVENTION

This invention is directed to the discovery of a novel class of 1-thiogalactose derivatives which inhibit the binding heat-labile enterotoxin (LT) and/or cholera toxin (CT) to an LT and/or CT receptor. The compounds of this invention also inhibit binding of *Vibrio cholerae* and enterotoxigenic strains of *Escherichia coli* can directly bind to cell surface receptors. The novel class of compounds provided by this invention is defined by formula I below:

$$\text{I}$$

wherein $R^1$ is selected from the group consisting of hydrogen, alkyl, substituted allyl, alkenyl, alkaryl, alkoxyalkyl, aryl, cycloalkyl, cycloalkenyl, heteroaryl, heterocyclic and thioalkoxyalkyl;

$R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

$R^3$ is selected from the group consisting of hydrogen, alkyl, substituted alkyl, alkenyl alkaryl, alkoxyalkyl, aryl, cycloalkyl, cycloalkenyl, heteroaryl, heterocyclic and thioalkoxyalkyl; wherein $R^1$ and $R^2$ or $R^1$ and $R^3$ or $R^2$ and $R^3$ can be joined, together with the carbon atoms to which $R^1$ and/or $R^2$ and/or $R^3$ are attached, to form a cycloalkyl ring, a cycloalkenyl ring, or a heterocyclic ring;

$R^4$ is selected from the group consisting of —$XR^5$, —$XC(O)R^6$, —$XC(O)X'R^7$ and —$C(O)XR^8$;

wherein X and X' are each independently selected from the group consisting of oxygen, sulfur and —$NR^9$—, wherein $R^9$ is selected from the group consisting of hydrogen and alkyl;

$R^5$ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is —$NR^9$—, then $R^9$ together with X can form an amino acid;

$R^6$ is selected from the group consisting of alkyl, alkenyl, aralkyl, alkoxyalkyl, aryl, cycloalkyl, cycloalkenyl, heteroaryl, heterocyclic and thioalkoxyalkyl;

$R^7$ is selected from the group consisting of alkyl, alkenyl, alkaryl, alkoxyalkyl, aryl, cycloalkyl, cycloalkenyl, heteroaryl, heterocyclic and thioalkoxyalkyl;

$R^8$ is selected from the group consisting of alkyl, alkenyl, alkaryl, alkoxyalkyl, aryl, cycloalkyl, cycloalkenyl, heteroaryl, heterocyclic and thioalkoxyalkyl; and n is an integer equal to 0 or 1;

with the provisos that:

when $R^1$ and $R^2$ are joined, together with the carbon atoms to which they are attached, to form a cyclohexyl ring, $R^4$ is —$XR^5$, X is oxygen and n is 0, then $R^5$ is not hydrogen;

when $R^1$ and $R^2$ are joined, together with the carbon atoms to which they are attached, to form a cyclohexyl ring, $R^4$ is —$XC(O)R^6$, X is —NH— and n is 0, then $R^6$ is not 2-carboxyphenyl;

when $R^1$ and $R^2$ are joined, together with the carbon atoms to which they are attached, to form a cyclohexyl ring, $R^4$ is —$XR^5$, X is —$NR^9$— and n is 0, then X and $R^5$ together do not form the amino acid L-leucine;

when $R^1$ and $R^2$ are joined, together with the carbon atoms to which $R^1$, $R^2$ and $R^3$ are attached, to form a cyclopentyl or cycloheptyl ring, $R^3$ is hydrogen, $R^4$ is —$XR^5$, X is oxygen and n is 1, then $R^5$ is not hydrogen;

when $R^1$ and $R^2$ are joined, together with the carbon atoms to which $R^1$, $R^2$ and $R^3$ are attached, to form a cyclohexyl ring, $R^3$ is hydrogen, $R^4$ is —$C(O)R^6$, X is —NH— and n is 1, then $R^6$ is not methyl.

In formula I above, when n is 0, $R^1$ and $R^2$ are preferably joined, together with the carbon to which they are attached, to form a cyclopentane or cyclohexane ring. When n is 1, $R^1$ and $R^2$ are preferably joined, together with the carbon atoms to which $R^1$, $R^2$ and $R^3$ are attached, to form a cyclopentane, cyclohexane, or cycloheptane ring; or $R^2$ and $R^3$ are preferably joined, together with the carbon atoms to which they are attached, to form a bicyclo[2.2.1]heptane ring.

When $R^3$ is not joined with $R^2$ to form a cycloalkyl ring, $R^3$ is preferably hydrogen.

Preferred $R^4$ groups include, by way of example, those having the formula —$XR^5$ where X and $R^5$ form an amino group, a hydroxy group or an amino acid selected from the group consisting of glycine, β-alanine, leucine and tryptophan; or those having the formula —$XC(O)R^6$ where X is —NH— and $R^6$ is methyl or (2-carboxyphenyl).

Particularly preferred compounds provided by this invention include, by way of example, the following:

2-hydroxycyclopentyl 1-thio-β-D-galactopyranoside (A1)
(2-hydroxybicyclo[2.2.1]cycloheptyl)methyl 1-thio-β-D-galactopyranoside (A4)
5,5-dimethyl-3-hydroxycyclopentyl 1-thio-β-D-galactopyranoside (A6)
6,6-dimethyl-3-hydroxycyclohexyl 1-thio-β-D-galactopyranoside (A9)
3-hydroxycyclohexyl 1-thio-β-D-galactopyranoside (A10)
2-aminocyclopentyl 1-thio-β-D-galactopyranoside (B1)
2-aminocyclohexyl 1-thio-β-D-galactopyranoside (B2)
(2-aminobicyclo[2.2.1]cycloheptyl) methyl 1-thio-β-D-galactopyranoside (B4)
3-aminocycloheptyl 1-thio-β-D-galactopyranoside (B5)
5,5-dimethyl-3-aminocyclopentyl 1-thio-β-D-galactopyranoside (B6)
3-aminocyclopentyl 1-thio-β-D-galactopyranoside (B7)
3-aminocyclohexyl 1-thio-β-D-galactopyranoside (B10)
2-acetamidocyclohexyl 1-thio-β-D-galactopyranoside (C2)
3-acetamidocycloheptyl 1-thio-β-D-galactopyranoside (C5)
3-acetamidocyclopentyl 1-thio-β-D-galactopyranoside (C7)
(2-(carboxybenzamido)bicyclo[2.2.1]cycloheptyl)methyl 1-thio-β-D-galactopyranoside (D4)
3-(2-carboxybenzamido)cycloheptyl 1-thio-β-D-galactopyranoside (D5)
6,6-dimethyl-3-(2-carboxybenzamido)cyclohexyl 1-thio-3-D-galactopyranoside (D9)
$N^\alpha$-[1-(1-thio-β-D-galactopyranosyl)cyclohex-2-yl1-glycine (E2)
$N^\alpha$-[1-(1-thio-β-D-galactopyranosyl)methyl)bicyclo[2.2.1]hept-2-yl]-glycine (E4)
$N^\alpha$-[1-(1-thio-β-D-galactopyranosyl)cyclohept-3-yl]-glycine (E5)
$N^\alpha$-[1-(1-thio-β-D-galactopyranosyl)-6,6-dimethylcyclohex-3-yl]-glycine (E9)
$N^\alpha$-[1-(1-thio-β-D-galactopyranosyl)cyclohex-3-yl]-glycine (E10)
$N^\beta$-[1-(1-thio-β-D-galactopyranosyl)cyclopent-2-yl]-β-alanine (F1)
$N^\beta$-[1-(1-thio-β-D-galactopyranosyl)cyclohept-3-yl]-β-alanine (F5)
$N^\beta$-[1-(1-thio-β-D-galactopyranosyl)cyclopent-3-yl]-β-alanine (F7)
$N^\beta$-[1-(1-thio-β-D-galactopyranosyl)-6,6-methylcyclohex-3-yl]-β-alanine (F9)
$N^\beta$-[1-(1-thio-β-D-galactopyranosyl)cyclohex-3-yl]-β-alanine (F10)
$N^\alpha$-[1-(1-thio-β-D-galactopyranosyl)cyclohept-3-yl]-L-leucine (G5)
$N^\alpha$-[1-(1-thio-β-D-galactopyranosyl)-6,6-dimethylcyclohex-3-yl]-L-leucine (G9)
$N^\alpha$-[1-(1-thio-β-D-galactopyranosyl)cyclohex-3-yl]-L-leucine (G10)
$N^\alpha$-[1-(1-thio-β-D-galactopyranosyl)cyclohex-2-yl]-L-histidine (H2)
$N^\alpha$-[1-(1-thio-β-D-galactopyranosyl)cyclohept-3-yl]-L-histidine (H5)
$N^\alpha$-[1-(1-thio-β-D-galactopyranosyl)-6,6-dimethylcyclohex-3-yl]-L-histidine (H9)
$N^\alpha$-[1-(1-thio-β-D-galactopyranosyl)cyclohex-3-yl]-L-histidine (H10)
$N^\alpha$-[1-(1-thio-β-D-galactopyranosyl)cyclohex-2-yl]-L-tryptophan (I2)
$N^\alpha$-[1-(1-thio-β-D-galactopyranosyl)cyclohept-3-yl]-L-tryptophan (I5)
$N^\alpha$-[1-(1-thio-β-D-galactopyranosyl)-6,6-dimethylcyclohept-3-yl]-L-tryptophan (I9)
$N^\alpha$-[1-(1-thio-β-D-galactopyranosyl)cyclohept-3-yl]-L-tryptophan (I10)
$N^\alpha$-[1-(1-thio-β-D-galactopyranosyl)cyclohex-2-yl]-L-arginine (J2)
$N^\alpha$-[1-(1-thio-β-D-galactopyranosyl)cyclohept-3-yl]-L-arginine (J5)
$N^\alpha$-[1-(1-thio-β-D-galactopyranosyl)cyclopent-3-yl]-L-arginine (J7)
$N^\alpha$-[1-(1-thio-β-D-galactopyranosyl)cyclopent-2-yl]-glycine (E1)
$N^\beta$-[1-(1-thio-β-D-galactopyranosyl)cyclohex-2-yl]-β-alanine (F2)
4,4-dimethyl-3-hydroxycyclohexyl 1-thio-β-D-galactopyranoside (A8)
3-amino-4,4-dimethylcyclohexyl 1-thio-β-D-galactopyranoside (B8)
3-acetamido-4,4-dimethylcyclohexyl 1-thio-β-D-galactopyranoside (C8)
$N^\alpha$-[1-(1-thio-β-D-galactopyranosyl)-4,4-dimethylcyclohex-3-yl]-β-glycine (E8)
$N^\beta$-[1-(1-thio-β-D-galactopyranosyl)-4,4-methylcyclohex-3-yl]-β-alanine (F8)

DETAILED DESCRIPTION OF THE INVENTION

Figure 1:
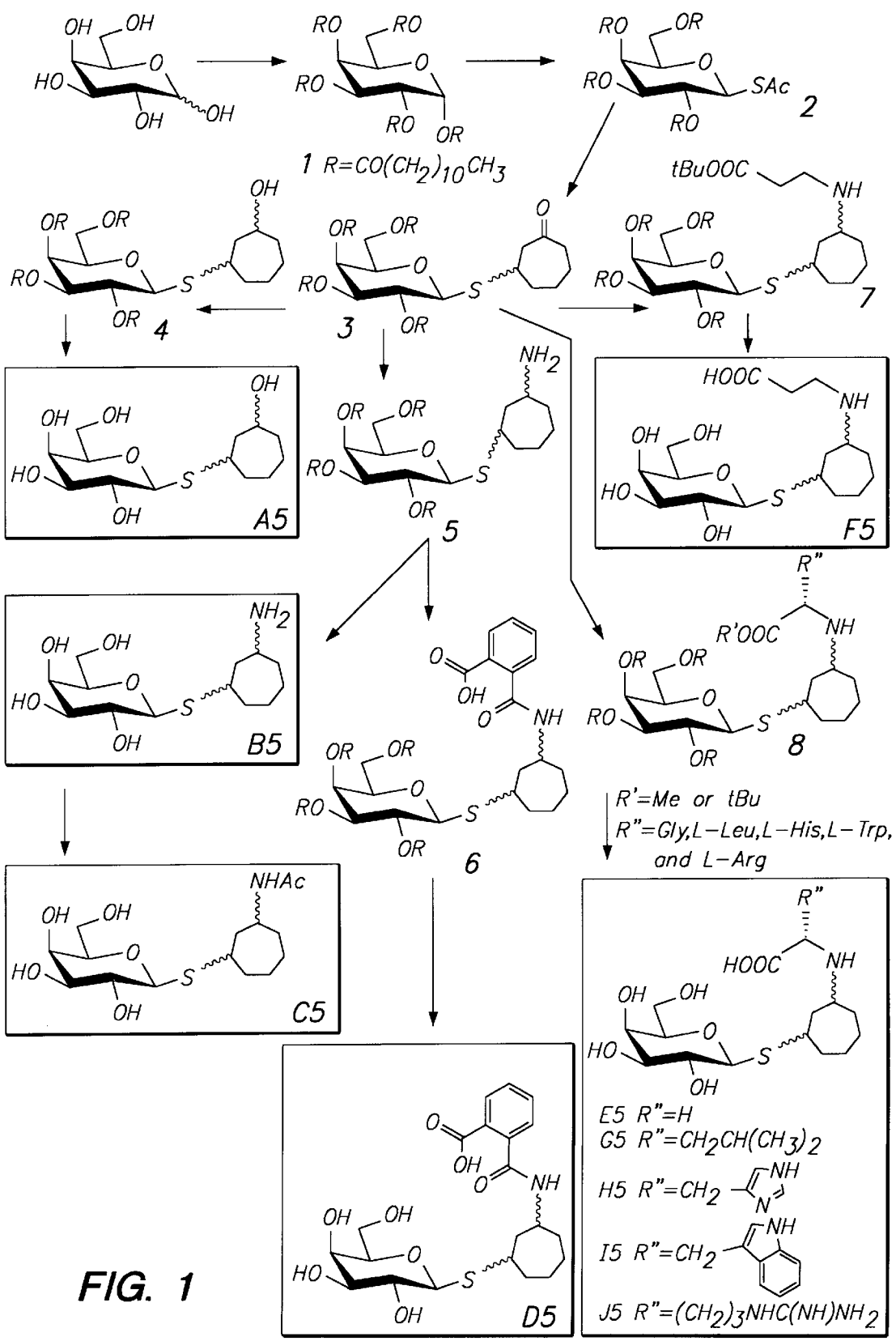
FIG. 1 illustrates a preferred reaction scheme which can be used to prepare various 1-thiogalactose derivatives from an α,β-unsaturated carbonyl compound, i.e., cyclohept-2-en-1-one.

This invention relates, in one embodiment, to compounds which inhibit the binding of heat labile toxin and/or chlorea toxin to cell surface receptors either in vitro or in viva. In another embodiment, the compounds of this invention inhibit binding of enterovirulent microorganisms (e.g., bacteria, virus, fungi, and the like) such as *Vibrio cholerae* and enterotoxigenic strains of *Escherichia coli* to cell surface receptors. However, prior to describing this invention in further detail, the following terms will first be defined.

Definitions

"Acyl" refers to the groups alkyl-C(O)—, aryl-C(O)—, and heteroaryl-C(O)— where alkyl, aryl and heteroaryl are as defined herein.

"Acylamino" refers to the group —C(O)NRR where each R is independently hydrogen or alkyl.

"Acyloxy" refers to the groups alkyl-C(O)O—, aryl—C(O)O—, heteroaryl-C(O)O—, and heterocyclic-C(O)O— where alkyl, aryl, heteroaryl and heterocyclic are as defined herein.

"Alkaryl" refers to -alkylene-aryl groups preferably having from 1 to 8 carbon atoms in the alkylene moiety and from 6 to 10 carbon atoms in the aryl moiety. Such alkaryl groups are exemplified by benzyl, phenethyl and the like.

"Alkoxy" refers to the group alkyl-O—. Such alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxyalkyl" refers to the group -alkylene-O-alkyl which includes by way of example, methoxymethyl ($CH_3OCH_2$—), methoxyethyl ($CH_3$—O—$CH_2CH_2$—) and the like.

"Alkenyl" refers to alkenyl groups preferably having from 2 to 8 carbon atoms and more preferably 2 to 6 carbon atoms and having at least 1 and preferably from 1–2 sites of alkenyl unsaturation. Such alkenyl groups include ethenyl (—CH=$CH_2$), n-propenyl (i.e., allyl) (—$CH_2$CH=CH2), iso-propenyl (—C($CH_3$)=$CH_2$), and the like.

"Alkyl" refers to monovalent alkyl groups preferably having from 1 to 8 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to a branched or straight chain alkyl group of from 1 to 8 carbon atoms having from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy, and the like. Preferred substituents include hydroxy and amino.

"Alkylene" refers to divalent alkylene groups preferably having from 1 to 8 carbon atoms and more preferably 1 to 6 carbon atoms. This term is exemplified by groups such as methylene (—$CH_2$—), ethylene (—$CH_2CH_2$—), the propylene isomers (e.g., —$CH_2CH_2CH_2$— and —CH($CH_3$)$CH_2$—) and the like.

"Alkynyl" refers to alkynyl groups preferably having from 2 to 8 carbon atoms and more preferably 2 to 6 carbon atoms and having at least 1 and preferably from 1–2 sites of alkynyl unsaturation. Such alkynyl groups include ethynyl (—CH≡$CH_2$), propargyl (—$CH_2$CH≡$CH_2$) and the like.

"Amino acid" refers to any of the naturally occurring amino acids, as well as synthetic analogs and derivatives thereof. α-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). One of skill in the art will appreciate that the term "amino acid" can also include β-, γ-, δ-, and ω-amino acids, and the like. Unnatural amino acids are also known in the art, as set forth in, for example, Williams[3], Evans et al.[4], Pu et al.[5], Williams et al.[6], and all references cited therein. Stereoisomers (e.g., D-amino acids) of the twenty conventional amino acids, unnatural amino acids such as α,α-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy.

"Aryloxy" refers to the group aryl-O— where the aryl group is as defined herein including optionally substituted aryl groups as also defined herein.

"Carboxy" refers to the group —COOH.

"Carboxyalkyl" refers to the group —C(O)O-alkyl where alkyl is as defined herein.

"Cycloalkyl" refers to cyclic alkyl groups or cyclic alkyl rings of from 3 to 8 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like. Examples of suitable cycloalkyl rings include single ring structures such as cyclopentane, cyclohexane, cycloheptane, cyclooctane, and the like, or multiple ring structures such as bicyclo[2.2.1]heptane, bicyclo[3.2.1]octane, and the like. Preferred cycloalkyl rings include cyclopentane, cyclohexane, cycloheptane and bicyclo[3.2.1]octane.

"Cycloalkenyl" refers to cyclic alkenyl groups or cyclic alkenyl rings of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2enyl, cyclopent-3-enyl, cyclooct-3-enyl and the like. Such cycloalkenyl rings include, by way of example, cyclopentene, cyclohexene, and the like.

"Halo" or "halogen" refers to fluoro, chloro, bromo and iodo and preferably is either chloro or bromo.

"α-Halocarbonyl compound" refers to a compound having the general formula: W—CHR$^1$—C(O)R$^2$ wherein R$^1$ and R$^2$ are as defined herein, and W is chloro, bromo or iodo. Such a-halocarbonyl compounds include, by way of example, α-chloroaldehydes, α-bromoaldehydes, α-iodoaldehydes, α-chloroketones, α-bromoketones, α-iodoketones and the like.

"Heteroaryl" refers to a monovalent aromatic carbocyclic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, alkoxy, aryl, aryloxy, halo, nitro, heteroaryl, thioalkoxy, thioaryloxy and the like. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heteroaryl groups can have a single ring (e.g., pyrrolidinyl, pipridinyl, morpholinyl or tetrahydrofuranyl) or multiple condensed rings (e.g., indolinyl).

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline and the like.

"Michael acceptor" refers to an α,β-unsaturated carbonyl compound having the general formula (II):

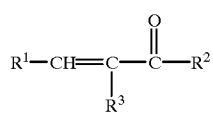

II wherein R$^1$, R$^2$ and R$^3$ are as defined herein; or R$^1$CH=CR$^2$—C(O)XR$^8$, wherein R$^1$, R$^2$, R$^8$ and X are as defined herein. Such Michael acceptors include, by way of example, α,β-unsaturated aldehydes, α,β-unsaturated ketones, α,β-unsaturated esters, α,β-unsaturated thioesters, α,β-unsaturated amides and the like.

"Thioalkoxyalkyl" refers to the group -alkylene-S-alkyl which includes by way of example, thiomethoxymethyl ($CH_3SCH_2$—), thiomethoxyethyl ($CH_3$—S—$CH_2CH_2$—) and the like.

"Thiol" refers to the group —SH.

"Thioalkoxy" refers to the group —S-alkyl wherein the alkyl group is as defined herein.

"Thioaryloxy" refers to the group aryl-S— wherein the aryl group is as defined herein, including optionally substituted aryl groups as also defined herein.

"Thioheteroaryloxy" refers to the group heteroaryl-S— wherein the heteroaryl group is as defined herein, including optionally substituted heteroaryl groups as also defined herein.

The terms "heat-labile enterotoxin" or "LT" refer to an enterotoxin of enterotoxigenic *E. coli* which initiates traveller's diarrhea and related conditions. This toxin has a lectin-like activity.

The term "traveller's diarrhea" refers to diarrhea of sudden onset, often accompanied by abdominal cramps, vomiting and fever that occurs sporadically in traveller's, usually during the first week of a trip. This diarrhea is most commonly caused by enterotoxigenic *E. coli*.

The term "cholera" refers to an acute epidemic infectious disease caused by *Vibrio cholerae*, wherein a soluble toxin elaborated in the intestinal tract by the Vibrio alters the permeability of the mucosa, causing a profuse watery diarrhea, extreme loss of fluid and electrolytes, and a state of dehydration and collapse, but no gross morphologic change in the intestinal mucosa.

The terms "cholera toxin" or "CT" refer to an enterotoxin of *V. cholerae* which initiates cholera and related conditions. This toxin has a lectin-like activity.

The phrase "inhibit(s) the binding of heat-labile enterotoxin (LT) and/or cholera toxin (CT) to an LT and/or CT receptor" means that a compound inhibits the binding of LT and/or CT to an LT and/or CT receptor, such as ganglioside $G_{D1b}$ or ganglioside $G_{M1}$, by at least 20% at a concentration of 2 mg/mL under conditions where thiodigalactoside (α-Gal-S-αGal) inhibits binding to the receptor by 20%. Such binding is reported herein as percent toxin activity remaining so that those compounds which result in about 80% or less toxin activity remaining under the bioassay conditions disclosed herein are deemed to inhibit the binding of LT and/or CT to the LT and/or CT receptor.

For purpose of this application, all sugars are referenced using conventional three letter nomenclature. All sugars are assumed to be in the D-form unless otherwise noted, except for fucose, which is in the L-form. Further, all sugars are in the pyranose form.

When chiral centers are found in the 1-thiogalactose derivatives of this invention other than the chiral centers of the galactose moiety, this invention encompasses all possible steroisomers. For example, when n is 0 in formula I, the carbon atoms to which R$^1$ and R$^2$ are attached may have an R,R or R,S or S,R or S,S configuration. Similarly, when n is 1, the carbon atoms to which R$^1$, R$^2$ and R$^3$ are attached may have an R,R,R or S,R,R or R,S,R or R,R,S or S,S,R or S,R,S or R,S,S or S,S,S configuration.

General Synthetic Procedures

The 1-thiogalactose derivatives of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The 1-thiogalactose derivatives of this invention are typically prepared by reaction of a 2,3,4,6-tetra-O-protected 1-thiogalactose intermediate with an α,β-unsaturated carbonyl compound or an α-halocarbonyl compound. The resulting carbonyl-containing intermediate is then reduced or reductively amiiated to give an alcohol or an amine compound. Optionally, these alcohol or amine compounds can be further derivatized by reaction with, for example, acyl halides, acyl anhydrides, halo formates and isocyanates to afford esters, amides, carbonates, ureas and the like. Such derivatization reactions of alcohols and amines are well known to those of ordinary skill in the art and can be accomplished using art recognized procedures.

The α,β-unsaturated carbonyl compounds employed in preparing the 1-thiogalactose derivatives of this invention have the general formula (II):

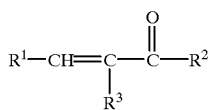

II wherein $R^1$, $R^2$ and $R^3$ are as defined above; or $R^1CH=CR^2-C(O)XR^8$, wherein $R^1$, $R^2$, $R^8$ and X are as defined above. These compounds are either commercially available or can be prepared from commercially available materials using art recognized procedures. For example, such compounds can be prepared via a Wittig reaction from an aldehyde, $R^1CHO$, and a β-carbonyl phosphorane, such as $(Ph)_3PC(R^3)C(O)R^2$.

Preferred α,β-unsaturated carbonyl compounds for use in this invention include, by way of example, cyclopent-2-en-1-one, 4,4-dimethylcyclopent-2-en-1-one, cyclohex-2-en-1-one, 4,4-dimethylcyclohex-2-en-1-one, 6,6-dimethylcyclohex-2-en-1-one, cyclohept-en-1-one, and 3-methylene-2-norbomanone.

The α-halocarbonyl compounds employed in preparing the 1-thiogalactose derivatives of this invention have the general formula: $W-CHR^1-C(O)R^2$ wherein $R^1$ and $R^2$ are as defined above, and W is chloro, bromo or iodo. Such compounds are either commercially available or can be prepared from commercially available materials using art recognized procedures. Preferred α-halocarbonyl compounds for use in this invention include, by way of example, 2-chlorocyclopentanone and 2-chlorocyclohexanone.

Figure 2:
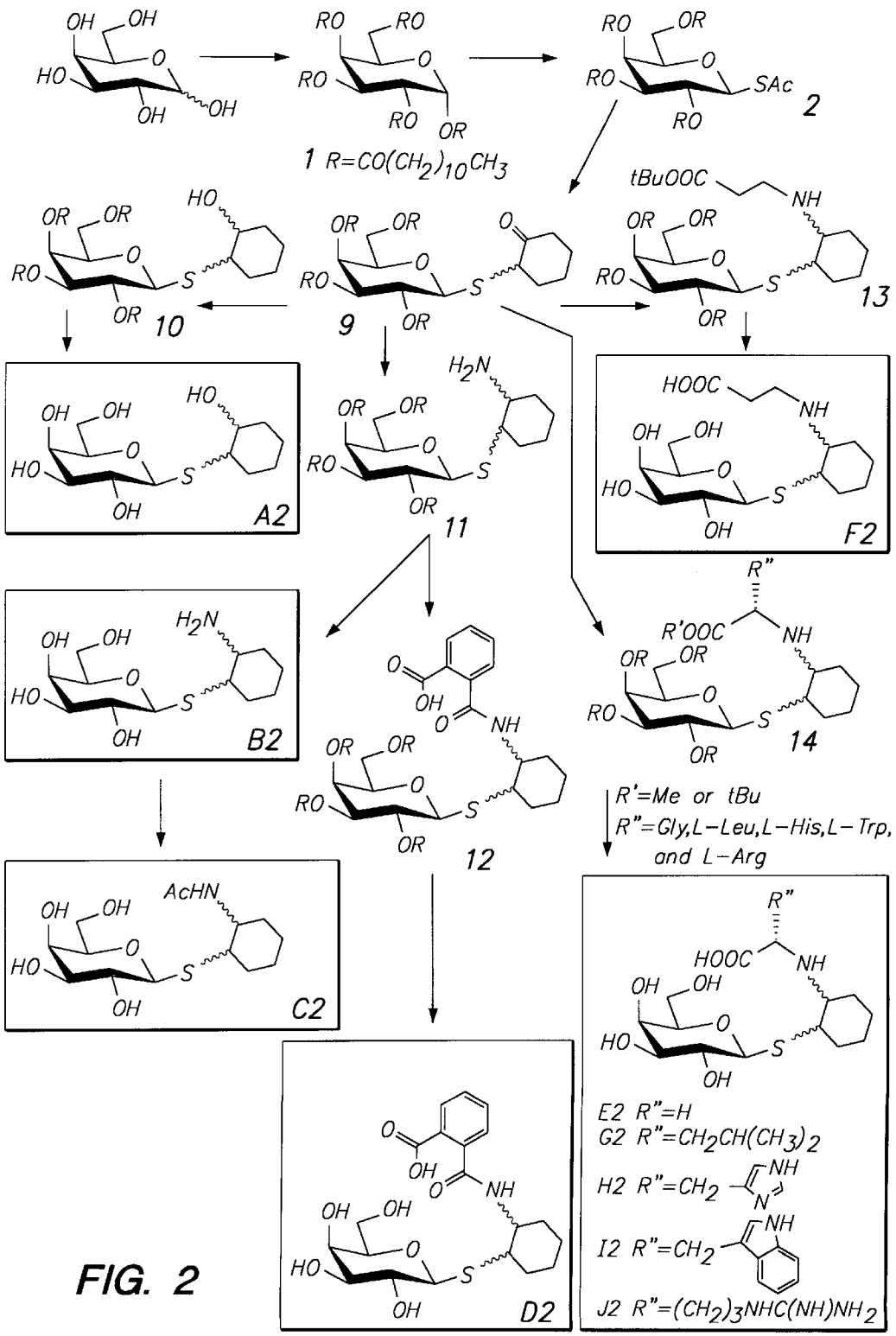
FIG. 2 illustrates a preferred reaction scheme which can be used to prepare various 1-thiogalactose derivatives from an α-halocarbonyl compound, i.e., 2-chlorocyclohexanone.

The synthesis of various 1-thiogalactose derivatives from either an α,β-unsaturated carbonyl compound or an α-halocarbonyl compound is illustrated in FIGS. 1 and 2, respectively. FIG. 1 illustrates the synthesis of various 1-thiogalactose derivatives from cyclohept-2-en-1-one. FIG. 2 illustrates the synthesis of various 1-thiogalactose from 2-chlorocyclohexanone. It will be readily apparent to those of ordinary skill in the art that the synthetic procedure illustrated in FIGS. 1 and 2 and following reaction conditions can be modified by selecting the appropriate starting materials and reagents to allow the preparation of other 1-thiogalactose derivatives of this invention.

As shown in FIG. 1, D-galactose is perlauroylated by contacting D-galactose with at least 5 equivalents, and preferably 10 equivalents, of lauroyl chloride. This reaction is generally conducted in an inert diluent, such pentane, hexane, dichloromethane and the like, using a tertiary amine such as pyridine or triethylamine to neutralize the hydrochloric acid generated during the reaction. Preferably, a catalytic amount of 4-(N,N-dimethylamino)pyridine is added to the reaction mixture to facilitate this reaction. Typically, this reaction is conducted at a temperature of from about −78° C. to about 30° C. for about 0.5 to about 96 hours to afford 1,2,3,4,6-penta-O-lauroyl-α-D-galactopyranose, 1, in approximately 70% yield from D-galactose.

Compound 1 is then converted into 1-S-acetyl-2,3,4,6-tetra-O-lauroyl-1-thio-α-D-galactopyranose, 2, by reaction of 1 with an excess of thiolacetic acid. Preferably, this reaction is conducted using about 10 equivalents of thiolacetic acid based on 1. The reaction is generally conducted in the presence of an excess of boron trifluoride etherate, preferably using about 15 to 20 equivalents of boron trifluoride etherate based on 1, in an inert diluent, such as dichloromethane and the like. Typically, this reaction is conducted initially at about 0° C. and then at about 30° C. for about 0.5 to about 48 hours.

Alternatively, compound 2 can be prepared from I by contacting 1 with at least one equivalent, preferably 1 to 1.2 equivalents, of benzylamine to selectively remove the 1-lauroyl group. This reaction is typically conducted at about 25° C. to about 30° C. for about 1 to about 96 hours to provide for 2,3,4,6-tetra-O-lauroyl-(α,β)-galactopyranoside. This intermediate is then converted into an O-(2,3,4,6-tetra-O-lauroyl-(α,β)-galactopyranosyl) trichloroacetimidate intermediate by contacting the tetralauroyl compound with an excess of trichloroacetonitrile, preferably about 10 equivalents, and about 0.8 to about 1.0 equivalents, of 1,8-diazabicyclo[5.4.0]undec-7-ene (DBU) in an inert diluent, such as dichloromethane. The resulting O-trichloroacetidate intermediate is then contacted with an excess of thiolacetic acid in an inert diluent, such as dichloromethane, at about 25° C. to about 30° C. for about 1 to about 96 hours to provide for 1-S-acetyl-2,3,4,6-tetra-O-lauroyl-1-thio-α-D-galactopyranose, 2.

The Michael addition of compound 2 to cyclohept-2-en-1-one then affords cycloheptanon-3-yl 2,3,4,6-tetra-O-lauroyl-1-thio-3-D-galactopyranoside, 3. This reaction is typically conducted by contacting 2 with at least one equivalent, preferably 1.0 to 1.2 equivalents, of cyclohept-2-en-1-one in the presence of a molar excess of a dialkylamine, such as diethylamine. Without being limited by any theory, it is believed that the dialkylamine first reacts with the thioacetyl of compound 2 thereby forming in situ the thiol derivative of compound 2 which then reacts under basic conditions generated by the dialkylamine with a Michael adduct.

Typically, this reaction is conducted in an inert diluent, such as dichloromethane, at a temperature of from about 40° C. to about 50° C. for about 1 to about 6 hours.

The carbonyl group of compound 3 can then reduced using a reducing agent to provide for 3-hydroxycycloheptyl 2,3,4,6-tetra-O-lauroyl-1-thio-3-D-galactopyranoside, 4. Preferably, this reduction is conducted by contacting 3 with sodium borohydride, preferably about 1.2 to about 2.0 equivalents of sodium borohydride based on 3. Generally, this reaction is conducted in an inert diluent, such as tetrahydrofuran, isopropanol and mixture thereof, at a temperature of about 25° C. to about 30° C. for about 0.5 to about 3.0 hours. The resulting alcohol, 4, is readily purified by solid-phase extraction on C18 silica gel using pentane as an eluent.

Removal of the lauroyl groups from alcohol 4 is then accomplished by treating 4 with an excess of sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides for 3-hydroxycycloheptyl 1-thio-β-galactopyranoside, A5.

Alternatively, compound 3 can be reductively aminated to provide for 3-aminocycloheptyl 2,3,4,6-tetra-O-lauroyl-1-thio-β-D-galactopyranoside, 5. In this reaction, compound 3 is contacted with an excess of ammonium acetate and at least one equivalent of sodium cyanoborohydride based on 3. This reaction is typically conducted in an inert diluent, such as methanol, tetrahydrofuran and mixtures thereof, at a temperature of about 25° C. to about 30° C. for about 1 to about 72 hours. The resulting amine compound 5 is readily purified by solid-phase extraction on C18 silica gel using pentane as an eluent.

Optionally, the amine group formed by reductive amination can be acylated with conventional acylating agents under conventional conditions. The acylating agent is generally of the formula L—C(O)R$^6$ where L is a leaving group such as a halide, an activated ester, and the like.

The lauroyl groups are removed from compound 5 by contacting 5 with an excess of sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides for 3-aminocycloheptyl 1-thio-β-galactopyranoside, B5.

In one example, the primary amine group of compound B5 can optionally be acylated by contacting B5 with an excess of acetic anhydride in methanol containing a trace of water. Generally, this reaction is conducted at about 25° C. to about 30° C. for about 2 to about 24 hours to provide for 3-acetamidocycloheptyl 1-thio-β-galactopyranoside, C5.

Alternatively, the primary amine group of 5 can be acylated with phthalic anhydride before removal of the lauroyl groups to provide for 3-(2-carboxybenzamido) cycloheptyl 2,3,4,6-tetra-O-lauroyl-1-thio-β-D-galactopyranoside, 6. This reaction is typically conducted by contacting compound 5 with at least one molar equivalent, preferably with an excess of phthalic anhydride. Preferably, this reaction is conducted in dry pyridine containing a catalytic amount of 4-(N,N-dimethylamino)pyridine. The reaction is typically conducted at about 25° C. to about 30° C. for about 12 to about 48 hours to provide for compound, 6. Removal of the lauroyl groups from 6 is then accomplished by treating 6 with sodium methoxide in methanol and an inert diluent, such as dichloromethane, at about 25° C. to about 30° C. for about 1 to about 24 hours. Neutralization of the reaction mixture with Amberlite IR-50 S (H$^+$) resin then provides for 3-(2-carboxybenzamido)cycloheptyl 1-thio-β-D-galactopyranoside, D5.

As shown in FIG. 1, compound 3 can also be reductively aminated with an amino acid ester to provide for intermediates 7 or 8. Specifically, compound 3 is contacted with a molar excess of β-alanine tert-butyl ester, preferably with 10 equivalents based on 3, in the presence of at least one molar equivalent, preferably about 1.0 to about 1.2 equivalents, of sodium cyanoborohydride. Typically, this reaction is conducted in an essentially anhydrous inert diluent, such as acetonitrile, at a temperature of about 25° C. to about 30° C. for about 1 to about 72 hours. The resulting intermediate 7 is readily purified by solid-phase extraction on C18 silica gel using pentane as the eluent.

The tert-butyl ester group of compound 7 is readily hydrolyzed to the corresponding carboxylic acid by treating 7 with an excess of trifluoroacetic acid in an inert diluent such as dichloromethane. This reaction is typically conducted at about 25° C. to about 30° C. for about 1 to about 10 hours. The lauroyl groups of the resulting carboxylic acid intermediate are then removed using sodium methoxide in methanol as described above to provide for N$^β$-[1-(1-thio-β-D-galactopyranosyl)cyclohept-3-yl]-β-alanine, F5.

In a similar manner, compound 3 can be reductively aminated using other amino acid esters, such as glycine tert-butyl ester, L-leucine tert-butyl ester, L-histidine methyl ester, L-tryptophan methyl ester, and L-arginine methyl ester, to provide for intermediate 8. In those cases where the amino acid ester employed is a tert-butyl ester, the tert-butyl ester is cleaved as described above using trifluoroacetic acid to afford N$^α$-[1-(1-thio-β-D-galactopyranosyl)cyclohept-3-yl]-glycine, E5, and N$^α$-[1-(1-thio-β-D-galactopyranosyl)cyclohept-3-yl]-L-leucine, G5. Alternatively, in those cases where an amino acid methyl ester is employed, the lauroyl groups of intermediate 8 are preferably removed before cleaving the methyl ester by treatment of 8 with sodium methoxide in methanol as described above. Subsequently, the methyl ester of the amino acid moiety is cleaved to the corresponding carboxylic acid by treatment with an excess of aqueous lithium hydroxide for about 0.5 to about 2 hours. Neutralization of the reaction mixture with Amberlite IR-50S (H$^+$) resin then provides for N$^α$-[1-(1-thio-β-D-galactopyranosyl)cyclohept-3-yl]-L-histidine, H5, N$^α$-[1-(1-thio-β-D-galactopyranosyl)cyclohept-3-yl]-L-tryptophan, I5, and N$^α$-[1-(1-thio-β-D-galactopyranosyl)cyclohept-3-yl]-arginine, J5.

As noted above, FIG. 2 illustrates the synthesis of various 1-thiogalactose derivatives using an α-halocarbonyl carbonyl compound, i.e., 2-chlorocyclohexanone. As shown in FIG. 2, 1-S-acetyl-2,3,4,6-tetra-O-lauroyl-1-thio-α-D-galactopyranose, 2, prepared as described above, reacts with 2-chlorocyclohexanone to give cyclohexanon-2-yl 2,3,4,6-tetra-O-lauroyl-1-thio-β-D-galactopyranoside, 9. This reaction is typically conducted by contacting 2 with at least one equivalent, preferably 1.0 to 1.2 equivalents, of 2-chlorocyclohexanone in the presence of an excess of a dialkylamine, such as diethylamine. Typically, this reaction is conducted in an inert diluent, such as dichloromethane, at a temperature of from about −40° C. to about 50° C. for about 1 to about 6 hours to afford compound 9.

Compound 9 can then be reacted using the same reagents and conditions described above for compound 3 to afford various 1-thiogalactose derivatives. Specifically, compound 9 is reduced with sodium borohydride to provide 10 which, after removal of the lauroyl groups, affords 2-hydroxycyclohexyl 1-thio-β-D-galactopyranoside, A2.

Alternatively, compound 9 is reductively aminated with ammonium acetate and sodium cyanoborohydride to provide for intermediate 11 which, upon removal of the lauroyl groups, affords 2-aminocyclohexyl 1-thio-β-D-galactopyranoside, B2. Compound B2 can then be acylated with acetic anhydride to give 2-acetamidocyclohexyl 1-thio-β-D-galactopyranoside, C2. Alternatively, intermediate 11 can be acylated with phthalic anhydride to provide for intermediate 12 which affords 2-(2-carboxybenzamidocyclohexyl 1-thio-β-D-galactopyranoside, D2, by removal of the lauroyl groups using the conditions described above.

Additionally, compound 9 can be reductively aminated using an alanine tert-butyl ester to provide for intermediate 13 which then affords N$^β$-[1-(1-thio-β-D-galactopyranosyl) cyclohex-2-yl]-β-alanine, F2, upon deprotection. Alternatively, compound 9 can be reductive aminated with other amino acid ester, such as glycine tert-butyl ester, L-leucine tert-butyl ester, L-histidine methyl ester, L-tryptophan methyl ester, and L-arginine methyl ester, to provide intermediate 14 which upon deprotection, affords N$^\alpha$-[1-(1-thio-β-D-galactopyranosyl)cyclohex-2-yl]-glycine E2, N$^\alpha$-[1-(1-thio-β-D-galactopyranosyl)cyclohex-2-yl]-L-leucine G2, N$^\alpha$-[1-(1-thio-β-D-galactopyranosyl) cyclohex-2-yl]-L-histidine H2, N$^\alpha$-[1(1-thio-β-D-galactopyranosyl)cyclohex-2-yl]-L-tryptophan 12, and N$^\alpha$-[1-(1-thio-β-D-galactopyranosyl)cyclohex-2-yl]-L-arginine J2.

In another embodiment, the 1-thiogalactose derivatives of this invention can be attached to a solid support either through the galactose moiety or through the portion of the molecule derived from the Michael acceptor or the α-halocarbonyl compound. Methods for attaching saccharides to solid supports are well known in the art and any of these known methods may be employed to covalently attach the 1-thiogalactose derivatives of this invention to a solid support.

Utility

In one embodiment, the compounds of this invention are useful in blocking binding of heat labile toxin and/or chlorea toxin to cell surface receptors either in vitro or in vivo. In another embodiment, the compounds of this invention inhibit binding of enterovirulent microorganisms (e.g., bacteria, virus, fungi, and the like) such as *Vibrio cholerae* and enterotoxigenic strains of *Escherichia coli*.

Accordingly, the compounds of this invention can be used to inhibit conditions associated with gastrointestinal infections caused by *Vibrio cholerae* and/or enterotoxigenic strains of *Escherichia coli* including by way of example diarrhea, intestinal bleeding, abdominal pain, and the like.

When used in inhibiting such conditions, the compounds of this invention are typically delivered to a patient in need of such treatment by a pharmaceutical composition comprising a pharmaceutically acceptable diluent and an effective amount of a compound of this invention. The amount of compound administered to the patient will vary depending upon what is being administered, the purpose of the administration, such as prophylaxis or therapy, the state of the patient, the manner of administration, and the like. In therapeutic applications, compositions are administered to a patient already suffering from gastrointestinal infections associated with *Vibrio cholerae* and/or enterotoxigenic strains of *Escherichia coli* in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of the infection in the patient, the age, weight and general condition of the patient, and the like. Preferably, for use as therapeutics, the compounds described herein are administered at dosages ranging from about 0.1 to about 10 mg/kg/day.

As noted above, the compounds administered to a patient are in the form of pharmaceutical compositions described above which can be administered by a variety of routes including oral, rectal, transdermal, subcutaneous, intravenous, intramuscular, etc. These compounds are effective as both injectable and oral deliverable pharmaceutical compositions. Such compositions are prepared in a manner well known in the pharmaceutical art and comprise at least one active compound.

The pharmaceutical compositions are formulated in the presence of a pharmaceutically acceptable carrier. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, etc., containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The following synthetic and biological examples are offered to illustrate this invention and are not to be construed in any way as limiting the scope of this invention. Unless otherwise stated, all temperatures are in degrees Celsius.

The following examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Å = | angstroms |
| bd = | broad doublet |
| bs = | broad singlet |
| d = | doublet |
| dd = | doublet of doublets |
| DMAP = | dimethylaminopyridine |
| eq. = | equivalents |
| g = | grams |
| L = | liter |
| m = | multiplet |
| meq = | milliequivalent |
| mg = | milligram |
| mL = | milliliter |
| mmol = | millimol |
| N = | normal |
| q = | quartet |
| quint. = | quintet |
| s = | singlet |
| t = | triplet |
| TFA = | trifluoroacetic acid |
| THF = | tetrahydrofuran |
| TLC = | thin layer chromatography |
| µL = | microliter |

[1]H-Nmr spectra were recorded with a Brueker AM-360 spectrometer and MALDI-TOF mass spectra were recorded with a HP G2020A (LD-TOF) instrument. Optical rotations were measured with a Perkin-Elmer 241 polarimeter. Reactions were monitored by TLC on Silica Gel FG254 (E. Merck, Darmstadt, Germany).

Example A

Solid-Phase Extraction of Lauroylated Intermediates

As indicated in the following examples, certain lauroylated reaction intermediates were purified by solid-phase extraction. In this purification procedure, the reaction mixture is concentrated, re-dissolved in methanol, and applied onto C18 silica (Waters Prep C18, 125 Å, 1 g per 20 mg lauroylated carbohydrate). The C18 silica is then washed with methanol (10 mL/g C18 silica) and the product is eluted with pentane (10 mL/g C18 silica). For L-arginine containing compounds, the reaction mixture is concentrated, re-dissolved in 70% methanol and applied onto C18 silica. The C18 silica is then washed with 70% methanol and the product is eluted with methanol. The resulting product contains no residual reagents as determined by TLC, $^1$H-nmr, or MALDI-TOF mass spectroscopy.

Example B 1,2,3,4,6-Penta-O-lauroyl-α-D-galactopyranose 1

To a suspension of galactose (3.78 g, 21.0 mmol), pyridine (50 mL), and 4-dimethylaminopyridine (cat.) in pentane (150 mL) under argon atmosphere, was added lauroyl chloride (50 mL, 210 mmol) at −78° C. The mixture was allowed to reach ambient temperature. The resulting white slurry slowly dissolved and a fine precipitate of pyridinium hydrochloride formed. After 40 h, the pyridinium hydrochloride was filtered off and the pentane solution was concentrated. Column chromatography (SiO$_2$, pentane/EtOAc 9:1) gave 1 (16.0 g, 70% yield), $[α]_D^{25}$+39° (c 0.9, CHCl$_3$). $^1$H-Nmr data (CHCl$_3$): δ 6.39 (d, 1H, J 2.4 Hz, H-1), 5.51 (br s, 1H, H-4), 5.35 (m, 2H, H-2 and H-3), 4.32 (br t, 1H, J 6.6 Hz, H-5), 4.08 (d, 2H, J 6.6 Hz, H-6a and H-6b), 2.39, 2.38, 2.30, 2.26 (4 t, 2H each, J 7.5 Hz, —CH$_2$CO—), 2.21 (m, 2H, —CH$_2$CO—), 0.88 (t, 15 H, J 7.0 Hz, —CH$_3$). Anal. Calcd for C$_{66}$H$_{122}$O$_{11}$: C, 72.2; H, 11.3. Found: C, 72.6; H, 11.5.

Example C

1-S-Acetyl-2,3,4,6-tetra-O-lauroyl-1-thio-a-D-galactopyranose 2

Method 1: To compound 1 (from Example B, 1 g, 0.91 mmol) and thiolacetic acid (0.4 mL, 9.1 mmol) in dry dichloromethane (5 mL) under argon at 0° C., was added boron trifluoride etherate (1.7 mL, 13.6 mmol). The coldbath was removed after 10 min and after 24 h the mixture was diluted with dichloromethane, washed with saturated sodium bicarbonate, dried over sodium sulfate, and concentrated. Column chromatography (SiO$_2$, pentane/Et2O/EtOAc 9:1:1) gave 2 (0.60 g, 70% yield).

Method 2: To compound 1 (from Example B, 276.5 mg, 0.253 mmol) in dry tetrahydrofuran (2.0 mL) under argon, was added benzylamine (27.9 μL, 0.255 mmol). The mixture was concentrated after 70 h. The residue was dissolved in dry dichloromethane (4.0 mL) under argon and then trichloroacetonitrile (250 μL, 2.5 mmol) and 1,8-diazabicyclo[5.4.0]undec-7-ene (30 μL, 0.2 mmol) were added. The mixture was concentrated after 3 h and the residue was flashed through a short column (SiO$_2$, pentane/EtOAc 19:1), then concentrated. To the residue in dry dichloromethane (3.5 mL) under argon, was added thiolacetic acid (1 mL). After 96 h, the reaction mixture was concentrated and the residue was purified by column chromatography (SiO$_2$, pentane, EtOAc 19:1) to give 2 (90 mg, 37% yield), $[α]_D^{25}$21° (c 1, CHCl$_3$). $^1$H-Nmr data (CHCl$_3$): δ 5.47 (d, 1H, J 3.4 Hz, H-4), 5.32 (t, 1H, J 10.0 Hz, H-2), 5.25 (d, 1H, J 10.0 Hz, H-1), 5.12 (dd, 1H, J 3.4 and 10.0 Hz, H-3), 4.08 (m, 3H, H-5, H-6a and H-6b), 2.14–2.43 (m, 8H, —CH$_2$CO—), 2.37 (s, 3H, —SAc), 0.88 (t, 15 H, J 7.0 Hz, —CH3). Anal. Calcd for C$_{56}$H$_{102}$O$_{10}$S: C, 69.5; H, 10.6; S, 3.3. Found: C, 69.4; H, 10.8; S, 3.5.

Example D

General Procedure for Michael Additions and α-Halocarbonyl Substitutions

To compound 2 (1 mmol) and an electrophile (1.2 mmol) in dry dichloromethane (8 mL) under argon, was added Et$_2$NH (4 mL). After 1–3 h, the mixture was concentrated and the residue was purified by column chromatography on SiO$_2$ by eluting with pentane/EtOAc. The products were characterized with $^1$H-nmr spectroscopy and MALDI-TOF mass spectroscopy.

Example E

General Procedure for Reduction to Alcohols

To the product from Example D (100 mol) in dry tetrahydrofuran (2.0 mL) and isopropanol (0.7 mL) under argon atmosphere, was added NABH, (150 μmol). After 0.5–3 h, the mixture was concentrated and the residue was purified according to the solid-phase extraction procedure of Example A. The product alcohols were characterized with $^1$H-nmr spectroscopy and MALDI-TOF mass spectroscopy.

Example F

General Procedure for Reductive Amination to a Primary Amine

To the product from Example D (100 μmol) and ammonium acetate (75 mg, 1 mmol) in dry methanol (2.3 mL) and tetrahydrofuran (0.9 mL) under argon, was added NaCNBH$_3$ (100 μmol). After 1–72 h, the mixture was concentrated and the residue purified according to the solid-phase extraction procedure of Example A. The product amines were characterized with $^1$H-nmr spectroscopy and MALDI-TOF mass spectroscopy.

Example G

General Procedure for Acylation of Primary Amines with Phthalic Anhydride

The O-lauroylated primary amine from Example F (100 μmol), phthalic anhydride (2.7 mmol), and 4-(N,N-dimethylamino)pyridine (catalytic) were dissolved in dry pyridine. The mixture was concentrated after 12–48 h and the residue purified according to the solid-phase extraction procedure of Example A. The product 2-carboxybenzamides were characterized with $^1$H-nmr spectroscopy and MALDI-TOF mass spectroscopy.

Example H

General Procedure for Reductive Amination with Amino Acids

To the product from Example D (100 μmol) and an amino acid tert-butyl ester hydrochloride or methyl ester hydrochloride (1 mmol) in dry MeCN (2.25 mL) and THF (0.75 mL), was added NaCN $_3$ (100 μmol). After 1–72 h, the mixture was concentrated and the residue was purified according to the solid-phase extraction procedure of Example A. The product N-alkylated amino acids were characterized with $^1$H-nmr spectroscopy and MALDI-TOF mass spectroscopy.

Example I

General Procedure for Deblocking of Alcohols

To the lauroylated alcohol from Example E (100 μmol) in dry methanol (7.1 mL) and dichloromethane (1.4 mL) under argon atmosphere, was added methanolic sodium methoxide (1 M, 50 μL). After 1–24 h, the mixture was neutralized with Amberlite IR-50S (H$^+$) resin, filtered and concentrated. The residue was dissolved in water and applied onto a column of C18 silica (Waters Prep C18, 125 Å, 5 g). The C18 silica was washed with water (50 mL), and the product was then eluted with 70% methanol (50 mL). The resulting alcohols were characterized with $^1$H-nmr spectroscopy and MALDI-TOF mass spectroscopy.

Example J

General Procedure for Deblocking of Primary Amines

To the O-lauroylated primary amine from Example F (100 μmol) in dry methanol (7.1 mL) and dichloromethane (1.4 mL) under argon, was added methanolic sodium methoxide (1 M, 50 μL). After 1–24 h, the mixture was neutralized with Amberlite IR-50S (H$^+$) resin, filtered and concentrated. The residue was dissolved in dichloromethane/methanol 2:1 and applied to a Waters SepPak Plus Longbody SiO$_2$ cartridge. The cartridge was washed with dichloromethane/methanol (2:1) and then the product was eluted with dichloromethane/methanol/water (5:5:1) (20 mL) and concentrated. The residue was dissolved in water and applied onto a column of C18 silica (Waters Prep C18, 125 Å, 5 g). The C18 silica was washed with water (50 mL) and then the product was eluted with methanol (50 mL). The resulting primary amines were characterized with 1H-nmr spectroscopy and MALDI-TOF mass spectroscopy.

Example K

General Procedure for N-Acetylation of Primary Amines

To the primary amine from Example J (100 μmol) in moist methanol (4.4 mL) was added acetic anhydride (0.4 mL). The mixture was concentrated after 2–24 h, re-dissolved in water and applied to a column of C18 silica (Waters Prep C18, 125 Å, 5 g). The C18 silica was washed with water (50 mL) and then the product was eluted with methanol (50 mL). The resulting acetamides were characterized with 1H-nmr spectroscopy and MALDI-TOF mass spectroscopy.

Example L

General Procedure for Deblocking of 2-Carboxybenzamides

To the O-lauroylated 2-carboxybenzamide from Example G (100 μmol) in dry methanol (7.1 mL) and dichloromethane (1.4 mL) under argon, was added methanolic sodium methoxide (1 M, 50 μL). After 1–24 h, the mixture was neutralized with Amberlite IR-50S (H$^+$) resin, filtered and concentrated. The residue was dissolved in dichloromethane/methanol (8:1) and applied to a Waters SepPak Plus Longbody SiO$_2$ cartridge. The cartridge was washed with dichloromethane/methanol (8:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL), and then the product was eluted with methanol (50 mL). The resulting 2-carboxybenzamides were characterized with $^1$H-nmr spectroscopy and MALDI-TOF mass spectroscopy.

Example M

General Procedure for Deblocking of N-Alkylated Glycine, β-Alanine, and L-Leucine Compounds The N-alkylated amino acid tert-butyl ester from Example H (100 μmol) was treated with trifluoroacetic acid (3.5 mL) in dry dichloromethane (3.5 mL) for 1–10 h. n-Propyl acetate (8 mL) and toluene (16 mL) were added and the mixture was concentrated, then co-concentrated twice with toluene. To the residue in dry methanol (7.1 mL) and dichloromethane (1.1 mL) under an argon atmosphere was added methanolic sodium methoxide (1 M, 200 μL). After 1–24 h, the mixture was neutralized with Amberlite IR-50S (H$^+$) resin, filtered and concentrated. The residue was dissolved in dichloromethane/methanol (9:1) and applied to a Waters SepPak Plus Longbody SiO$_2$ cartridge. The cartridge was washed with dichloromethane/methanol (9:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL) and then the product was eluted with 70% methanol (50 mL). The resulting N-alkylated glycine, β-alanine, and L-leucine compounds were characterized with $^1$H-nmr spectroscopy and MALDI-TOF mass spectroscopy.

Example N

General Procedure for Deblocking of N-Alkylated L-Histidine and L-Tryptophan Compounds To the N-alkylated amino acid methyl ester from Example H (100 μmol) in dry methanol (7.3 mL) and dichloromethane (1.1 mL) under an argon atmosphere was added methanolic sodium methoxide (1 M, 50 μL). After 1–24 h, the mixture was neutralized with Amberlite IR-50S (H$^+$) resin, filtered and concentrated. The residue was dissolved in 70% methanol and applied to a column of C18 silica (Waters Prep C18, 125 Å, 5 g) and then the product was eluted with 70% methanol (50 mL). To the residue in water (3.7 mL) was added aqueous lithium hydroxide (1M, 0.3 mL). After 0.5–2 h, the mixture was neutralized with Amberlite IR-50S (H$^+$) resin, filtered and concentrated. The residue was dissolved in dichloromethane/methanol (9:1) and applied to a Waters SepPak Plus Longbody SiO$_2$ cartridge. The cartridge was washed with dichloromethane/methanol (9:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL), and the product was eluted with 70% methanol (50 mL). The resulting N-alkylated L-histidine and L-tryptophan compounds were characterized with $^1$H-nmr spectroscopy and MALDI-TOF mass spectroscopy.

Example O

General Procedure for Deblocking of N-Alkylated L-Arginine Compounds

To the N-alkylated arginine methyl ester from Example H (100 μmol) in dry methanol (7.3 mL) and dichloromethane (1.1 mL) under an argon atmosphere was added methanolic sodium methoxide (1M, 50 µL). After 1–24 h, the mixture was neutralized with Amberlite IR-50S (H⁺) resin, filtered and concentrated. The residue was dissolved in 70% methanol and applied to a column of C18 silica and then the product was eluted with 70% methanol (50 mL). To the residue in water (3.7 mL) was then added aqueous lithium hydroxide (1M, 0.3 mL). After 0.5–2 h, the mixture was neutralized with Amberlite IR-50s (H⁺) resin, filtered and concentrated. The residue was dissolved in water and applied to column of C18 silica (Waters Prep C18, 125 Å, 5 g). The C18 silica was washed with water (50 mL) and then the product was eluted with 50% methanol (50 mL). The resulting N-alkylated L-arginine compounds were characterized with $^1$H-nmr spectroscopy and MALDI-TOF mass spectroscopy.

Example 1

Synthesis of 2-Hydroxycyclopentyl 1-Thio-β-D-galactopyranoside A1

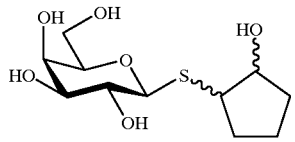

The title compound was prepared according to procedures D, E and I above using 2-chlorocyclopentanone as the electrophile. Mass spectra data was as follows: M (calcd.): 280.34; M (found): 304.9 (M+Na⁺). Selected nmr data was as follows: 1H-nmr (CD$_3$OD): δ 4.44, 4.43, 4.38, and 4.35 (4 d, J 10 Hz), 2.21, 1.99, 1.82, and 1.64 (4 m).

Example 2

Synthesis of 2-Hydroxycyclohexyl 1-Thio-β-D-galactopyranoside A2

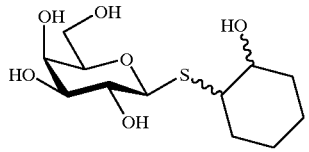

The title compound was prepared according to procedures D, E and I above using 2-chlorocyclohexanone as the electrophile. Mass spectra data was as follows: M (calcd.): 294.34; M (found): 318.8 (M+Na⁺).

Example 3

Synthesis of (2-Hydroxybicyclo[2.2.1]cycloheptyl)methyl 1-Thio-β-D-galactopyranoside A4

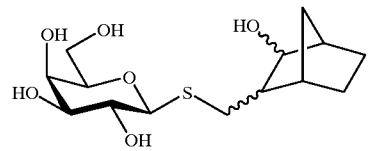

The title compound was prepared according to procedures D, E and I above using 3-methylene-2-norbornanone as the electrophile. Mass spectra data was as follows: M (calcd.): 320.41; M (found): 344.6 (M+Na⁺). Selected nmr data was as follows: 1H-nmr (CD$_3$OD): δ 4.32 and 4.31 (2 d, J 10 Hz), 3.89 (br d, J 3.5 Hz), 2.88 and 2.85 (2 dd, J 7 and 12 Hz), 2.69 and 2.67 (2 dd, J 10 and 12 Hz), 2.38 (br s), 2.05 (m), 1.85 (m), 1.58 (m), 1.33 (m).

Example 4

Synthesis of 3-Hydroxycycloheptyl 1-Thio-β-D-galactopyranoside A5

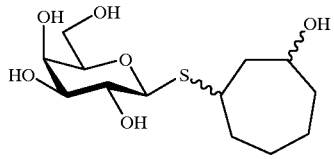

The title compound was prepared according to procedures D, E and I above using cyclohept-en-1-one as the electrophile. Mass spectra data was as follows: M (calcd.): 308.40; M (found): 332.1 (M+Na⁺).

Example 5

Synthesis of 5,5-Dimethyl-3-hydroxycyclopentyl 1-Thio-β-D-galactopyranoside A6

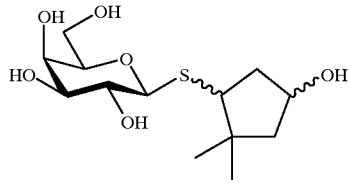

The title compound was prepared according to procedures D, E and I above using 4,4-dimethylcyclopent-2-en-1-one as the electrophile. Mass spectra data was as follows: M (calcd.): 308.40; M (found): 332.1 (M+Na⁺).

Example 6

Synthesis of 3-Hydroxycyclopentyl 1-Thio-β-D-galactopyranoside A7

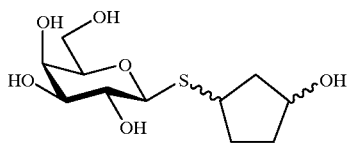

The title compound was prepared according to procedures D, E and I above using cyclopent-en-1-one as the electrophile. Mass spectra data was as follows: M (calcd.): 280.34; M (found): 304.9 (M+Na$^+$).

Example 7

Synthesis of 6,6-Dimethyl-3-hydroxycyclohexyl 1-Thio-β-D-galactopyranoside A9

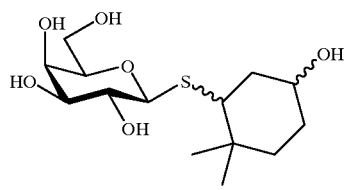

The title compound was prepared according to procedures D, E and I above using 4,4dimethylcyclohex-2-en-1-one as the electrophile. Mass spectra data was as follows: M (calcd.): 322.42; M (found): 346.6 (M+Na$^+$).

Example 8

Synthesis of 3-Hydroxycyclohexyl 1-Thio-β-D-galactopyranoside A10

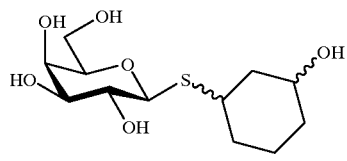

The title compound was prepared according to procedures D, E and I above using cyclohex-2-en-1-one as the electrophile. Mass spectra data was as follows: M (calcd.): 294.37; M (found): 318.3 (M+Na$^+$).

Example 9

Synthesis of 2-Aminocyclopentyl 1-thio-3-D-galactopyranoside B1

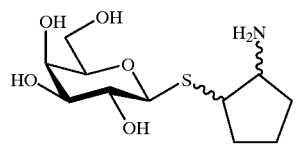

The title compound was prepared according to procedures D, F and J above using 2-chlorocyclopentanone as the electrophile. Mass spectra data was as follows: M (calcd.): 279.36; M (found): n.a. Selected nmr data was as follows: 1H-nmr (CD$_3$OD): δ 4.48, 4.46, 4.38, and 4.28 (4 d, J 10 Hz), 2.13, 1.75, and 1.59 (3 m).

Example 10

Synthesis of 2-Aminocyclohexyl 1-Thio-β-D-galactopyranoside B2

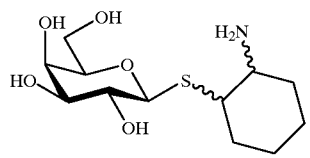

The title compound was prepared according to procedures D, F and J above using 2-chlorocyclohexanone as the electrophile. Mass spectra data was as follows: M (calcd.): 293.38; M (found): 295.8 (M+H$^+$), 319.7 (M+Na$^+$).

Example 11

Synthesis of (2-Aminobicyclo[2.2.1]cycloheptyl) methyl 1-Thio-β-D-galactopyranoside B4

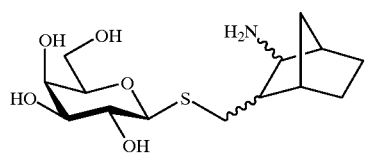

The title compound was prepared according to procedures D, F and J above using 3-methylene-2-norbornanone as the electrophile. Mass spectra data was as follows: M (calcd.): 319.42; M (found): 321.6 (M+H$^+$). Selected nmr data was as follows: 1H-nmr (CD$_3$OD): δ 4.42, 4.41, 4.38, and 4.35 (4 d, J 10 Hz), 2.35 (br s), 2.05 (m), 1.50 (m).

Example 12

Synthesis of 3-Aminocycloheptyl 1-Thio-β-D-galactopyranoside B5

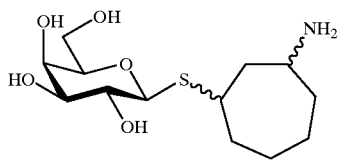

The title compound was prepared according to procedures D, F and J above using cyclohept-2-en-1-one as the electrophile. Mass spectra data was as follows: M (calcd.): 307.41; M (found): 333.0 (M+Na$^+$).

Example 13

Synthesis of 5,5-Dimethyl-3-aminocyclopentyl 1-Thio-β-D-galactopyranoside B6

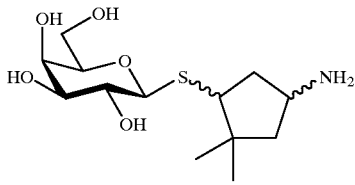

The title compound was prepared according to procedures D, F and I above using 4,4dimethylcyclopent-2-en-1-one as the electrophile. Mass spectra data was as follows: M (calcd.): 309.35; M (found): n.a. Selected nmr data was as follows: 1H-nmr (CD$_3$OD): δ 4.33, 4.32, 4.31, and 4.29 (4 d, J 10 Hz), 3.88 and 3.86 (2 br d, J 3.6 Hz), 1.63 (m), 1.15, 1.13, 1.11, 1.09, and 1.08 (5 s).

Example 14

Synthesis of 3-Aminocyclopentyl 1-Thio-β-D-galactopyranoside B7

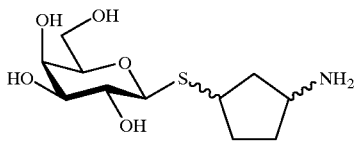

The title compound was prepared according to procedures D, F and J above using cyclopent-2-en-1-one as the electrophile. Mass spectra data was as follows: M (calcd.): 279.35; M (found): n.a. Selected nmr data was as follows: 1H-nmr (CD$_3$OD): δ 4.46, 4.40, 4.38, and 4.34 (4 d, J 10 Hz), 3.88 (br s), 2.61, 2.27, 2.15, 1.82, and 1.64 (5 m).

Example 15

Synthesis of 3-Aminocyclohexyl 1-Thio-β-D-galactopyranoside B10

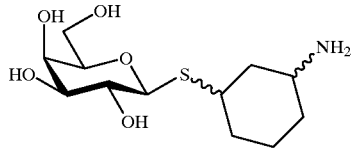

The title compound was prepared according to procedure D, F and J above using cyclohex-2-en-1-one as the electrophile. Mass spectra data was as follows: M (calcd.): 293.38; M (found): 316.2 (M+Na$^+$).

Example 16

Synthesis of 2-Acetamidocyclohexyl 1-Thio-β-D-galactopyranoside C2

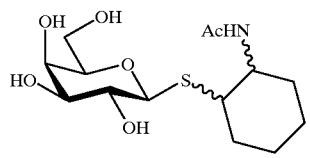

The title compound was prepared according to procedures D, F, J and K above using 2-chlorocyclohexanone as the electrophile. Mass spectra data was as follows: M (calcd.): 335.42; M (found): 359.4 (M+Na$^+$).

Example 17

Synthesis of 3-Acetamidocycloheptyl 1-Thio-β-D-galactopyranoside C5

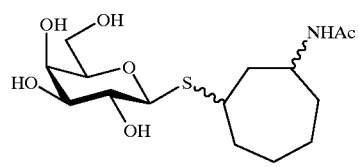

The title compound was prepared according to procedures D, F, J and K above using cyclohept-2-en-1-one as the electrophile. Mass spectra data was as follows: M (calcd.): 349.42; M (found): 372.5 (M+Na$^+$).

Example 18

Synthesis of 3-Acetamidocyclopentyl 1-Thio-β-D-galactopyranoside C7

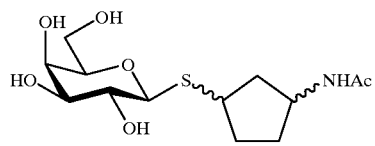

The title compound was prepared according to procedures D, F, J and K above using cyclopent-2-en-1-one as the electrophile. Mass spectra data was as follows: M (calcd.): 321.39; M (found): 349.5 (M+Na$^+$).

Example 19

Synthesis of 3-Acetamidocyclohexyl 1-Thio-β-D-galactopyranoside C10

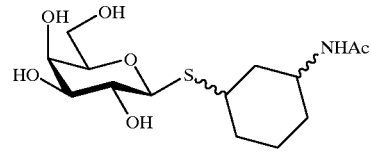

The title compound was prepared according to procedures D, F, J and K above using cyclohex-2-en-1-one as the electrophile. Mass spectra data was as follows: M (calcd.): 335.42; M (found): n.a. Selected nmr data was as follows: 1H-nmr (CD$_3$OD): δ 4.52, 4.46, and 4.45 (3 d, J 10 Hz), 3.90 (d, J 3.6 Hz), 2.96, 2.18, 1.94, 1.78, and 1.23 (5 m), 1.91, 1.92, 1.885, and 1.880 (4s).

Example 20

Synthesis of 2-(2-Carboxybenzamidocyclohexyl 1-Thio-β-D-galactopyranoside D2

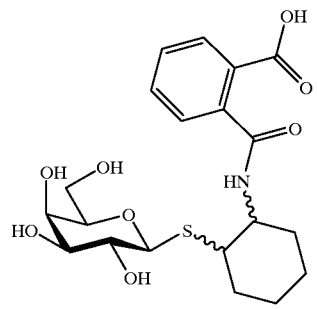

The title compound was prepared according to procedures D, F, G and L above using 2-chlorocyclohexanone as the electrophile. Mass spectra data was as follows: M (calcd.): 439.52; M (found): 465.9 (M+Na$^+$).

Example 21

Synthesis of (2-(Carboxybenzamido)bicyclo2.2.1] cycloheptyl)methyl 1-Thio-β-D-galactopyranoside D4

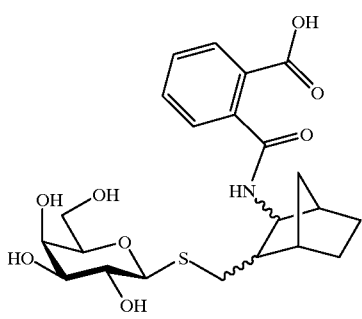

The title compound was prepared according to procedures D, F, G and L above using 3-methylene-2-norbornanone as the electrophile. Mass spectra data was as follows: M (calcd.): 467.54; M (found): 492.4 (M+Na$^+$). Selected nmr data was as follows: 1H-nmr (CD$_3$OD): δ 7.35–7.75 (m), 4.41, 4.35, 4.31, and 4.30 (4 d, J 10 Hz), 3.88 (br s), 2.40 (br s), 1.50 (m).

Example 22

Synthesis of 3-(2-Carboxybenzamido)cycloheptyl 1-Thio-β-D-galactopyranoside D5

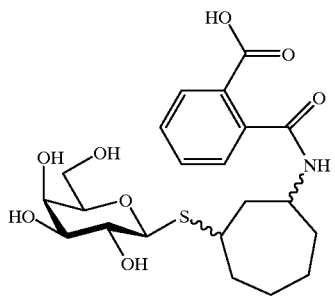

The title compound was prepared according to procedures D, F, G and L above using cyclohept-2-en-1-one as the electrophile. Mass spectra data was as follows: M (calcd.): 453.52; M (found): 479.6 (M+Na$^+$).

Example 23

Synthesis of 6,6-Dimethyl-3-(2-Carboxybenzamido) cyclohexyl 1-Thio-β-D-galactopyranoside D9

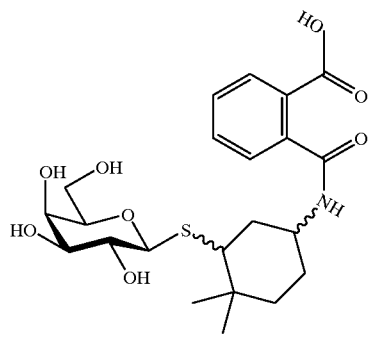

The title compound was prepared according to procedures D, F, G and L above using 4,4-dimethylcyclohex-2en-1-one as the electrophile. Mass spectra data was as follows: M (calcd.): 469.55, M (found): 492.4 (M+Na$^+$).

Example 24

Synthesis of N$^\alpha$-[1-(1-Thio-β-D-galactopyranosyl) cyclopent-2-yl]-glycine E1

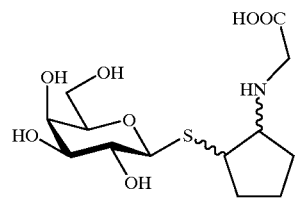

The title compound was prepared according to procedures D, H and M above using 2-chlorocyclopentanone as the electrophile and glycine tert-butyl ester as the amino acid ester. Mass spectra data was as follows: M (calcd.): 337.39; M (found): 363.4 (M+Na$^+$).

Example 25

Synthesis of N$^\alpha$[1-(1-Thio-β-D-galactopyranosyl)cyclohex-2-yl]-glycine E2

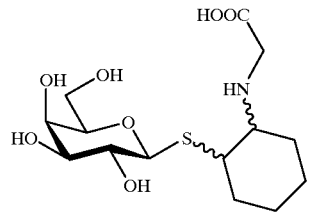

The title compound was prepared according to procedures D, H and M above using 2-chlorocyclohexanone as the electrophile and glycine tert-butyl ester as the amino acid ester. Mass spectra data was as follows: M (calcd.): 351.42; M (found): 353.5 (M+H$^+$), 376.5 (M+Na$^+$).

Example 26

Synthesis of N$^\alpha$-[1-((1-Thio-β-D-galactopyranosyl)methyl)bicyclo[2.2.1]hept-2-yl]-glycine E4

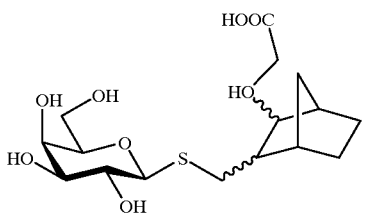

The title compound was prepared according to procedures D, H and M above using 3-methylene-2-norbornanone as the electrophile and glycine tert-butyl ester as the amino acid ester. Mass spectra data was as follows: M (calcd.): 377.46; M (found): 401.4 (M+Na$^+$). Selected nmr data was as follows: 1H-nmr (CD$_3$OD): δ 4.42, 4.40, 4.38, and 4.35 (4 d, J 10 Hz), 2.90 (2 s), 2.60 (br s), 2.42 (m), 1.50 (m).

Example 27

Synthesis of N$^\alpha$-[1-(1-Thio-β-D-galactopyranosyl)cyclohept-3-yl]-glycine E5

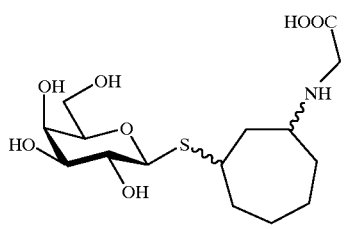

The title compound was prepared according to procedures D, H and M above using cyclohept-2-en-1-one as the electrophile and glycine tert-butyl ester as the amino acid ester. Mass spectra data was as follows: M (calcd.): 365.45; M (found): 367.4 (M+H$^+$), 389.9 (M+Na$^+$).

Example 28

Synthesis of N$^\alpha$-[1-(1-Thio-β-D-galactopyranosyl)-6,6-dimethylcyclohex-3-yl]-glycine E9

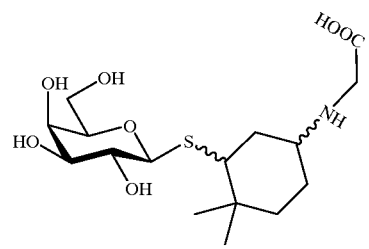

The title compound was prepared according to procedures D, H and M above using 4,4-dimethylcyclohex-2-en-1-one as the electrophile and glycine tert-butyl ester as the amino acid ester. Mass spectra data was as follows: M (calcd.): 379.47; M (found): 380.6 (M+H$^+$), 403.5 (M+Na$^+$).

Example 29

Synthesis of N$^\alpha$-[1-(1-Thio-β-D-galactopyranosyl)cyclohex-3-yl]-glycine E10

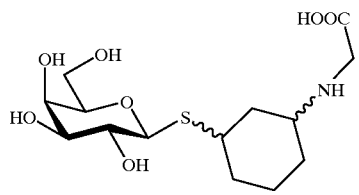

The title compound was prepared according to procedures D, H and M above using cyclohex-2-en-1-one as the electrophile and glycine tert-butyl ester as the amino acid ester. Mass spectra data was as follows: M (calcd.): 351.42; M (found): 375.5 (M+Na$^+$).

Example 30

Synthesis of N$^\beta$-[1-(1-Thio-β-D-galactopyranosyl)cyclopent-2-yl]-β-alanine F1

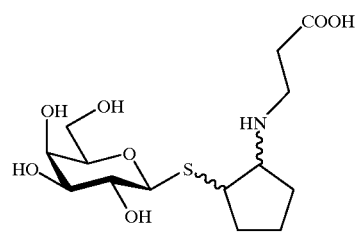

The title compound was prepared according to procedures D, H and M above using 2-chlorocyclopentanone as the electrophile and β-alanine tert-butyl ester as the amino acid ester. Mass spectra data was as follows: M (calcd.): 351.42; M (found): 353.3 (M+H$^+$), 375.5 (M+Na$^+$), 398.3 (M+K$^+$).

Example 31

Synthesis of N$^\beta$-[1-(1-Thio-$\beta$-D-galactopyranosyl) cyclohex-2-yl]-$\beta$-alanine F2

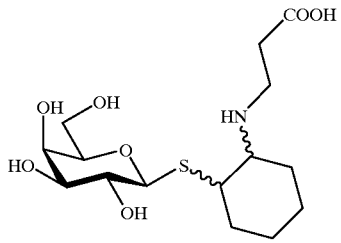

The title compound was prepared according to procedures D, H and M above using 2-chlorocyclohexanone as the electrophile and $\beta$-alanine tert-butyl ester as the amino acid ester. Mass spectra data was as follows: M (calcd.): 365.45; M (found): 367.4 (M+H$^+$), 389.9 (M+Na$^+$), 412.0 (M+K$^+$).

Example 32

Synthesis of N$^\beta$-[1-(1-Thio-$\beta$-D-galactopyranosyl) cyclohept-3-yl]-$\beta$-alanine F5

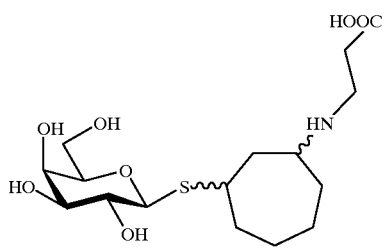

The title compound was prepared according to procedures D, H and M above using cyclohept-2en-1-one as the electrophile and 3-alanine tert-butyl ester as the amino acid ester. Mass spectra data was as follows: M (calcd.): 379.45; M (found): 381.7 (M+H$^+$), 403.5 (M+Na$^+$), 426.0 (M+K$^+$).

Example 33

Synthesis of N$^\beta$-[1-(1-Thio-$\beta$-D-galactopyranosyl) cyclopent-3-yl]-$\beta$-alanine F7

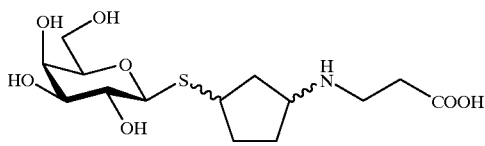

The title compound was prepared according to procedures D, H and M above using cyclopent-2-en-1-one as the electrophile and 3-alanine tert-butyl ester as the amino acid ester. Mass spectra data was as follows: M (calcd.): 351.42; M (found): n.a. Selected nmr data was as follows: 1H-nmr (CD$_3$OD): $\delta$ 4.41, 4.40, and 4.38 (3 d, J 10 Hz), 3.17 and 2.52 (2 br s), 2.21 and 1.94 (2 m).

Example 34

Synthesis of N$^\beta$-[1-(1-Thio-$\beta$-D-galactopyranosyl)-6,6-methylcyclohex-3-yl]-$\beta$-alanine F9

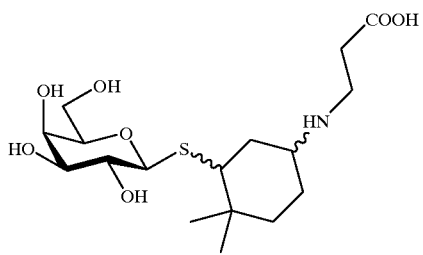

The title compound was prepared according to procedures D, H and M above using 4,4-dimethylcyclohex-2-en-1-one as the electrophile and $\beta$-alanine tert-butyl ester as the amino acid ester. Mass spectra data was as follows: M (calcd.): 393.50; M (found): 399.3 (M+H$^+$), 419.5 (M+Na$^+$), 442.4 (M+K$^+$).

Example 35

Synthesis of N$^\beta$-[1-(1-Thio-$\beta$-D-galactopyranosyl) cyclohex-3-yl]-$\beta$-alanine F10

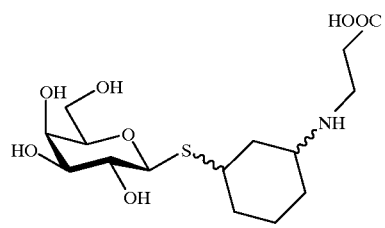

The title compound was prepared according to procedures D, H and M above using cyclohex-2-en-1-one as the electrophile and $\beta$-alanine tert-butyl ester as the amino acid ester. Mass spectra data was as follows: M (calcd.): 365.45; M (found): 389.9 (M+Na$^+$). Selected nmr data was as follows: 1H-nmr (CD$_3$OD): $\delta$ 4.45, 4.43, 4.42, and 4.36 (4 d, J 10 Hz), 3.18 and 2.47 (2 br s), 3.02, 2.56, 2.33, 2.07, 1.92, 1.81, 1.74, 1.50, and 1.34 (9 m).

Example 36

Synthesis of N$^\alpha$-[1-(1-Thio-$\beta$-D-galactopyranosyl) cyclohex-2-yl]-L-leucine G2

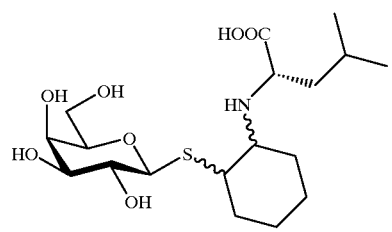

The title compound was prepared according to procedures D, H and M above using 2-chlorocyclohexanone as the electrophile and L-leucine tert-butyl ester as the amino acid ester. Mass spectra data was as follows: M (calcd.): 407.53; M (found): 410.9, (M+H$^+$), 435.5 (M+Na$^+$).

Example 37

Synthesis of N$^\alpha$-[1-(1-Thio-β-D-galactopyranosyl)cyclohept-3-yl]-L-leucine G5

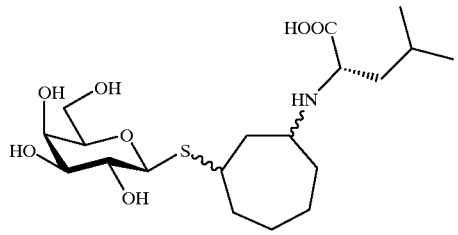

The title compound was prepared according to procedures D, H and M above using cyclohept-2-en-1-one as the electrophile and L-leucine tert-butyl ester as the amino acid ester. Mass spectra data was as follows: M (calcd.): 421.55; M (found): 421.7 (M+H$^+$), 448.0 (M+Na$^+$).

Example 38

Synthesis of N$^\alpha$-[1-(1-Thio-β-D-galactopyranosyl)-6,6-dimethylcyclohex-3-yl]-L-leucine G9

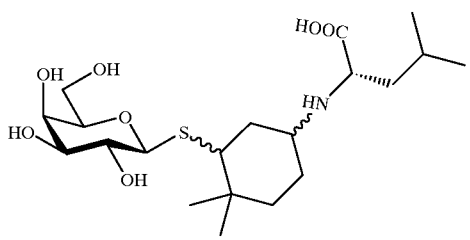

The title compound was prepared according to procedures D, H and M above using 4,4-dimethylcyclohex-2-en-1-one as the electrophile and L-leucine tert-butyl ester as the amino acid ester. Mass spectra data was as follows: M (calcd.): 436.58; M (found): 438.0 (M+H$^+$), 461.4 (M+Na$^+$).

Example 39

Synthesis of N$^\alpha$-[1-(1-Thio-β-D-galactopyranosyl)cyclohex-3-yl]-L-leucine G10

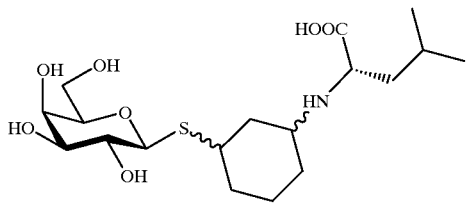

The title compound was prepared according to procedures D, H and M above using cyclohex-2en-1-one as the electrophile and L-leucine tert-butyl ester as the amino acid ester. Mass spectra data was as follows: M (calcd.): 407.53; M (found): 408.4 (M+H$^+$).

Example 40

Synthesis of N$^\alpha$-[1-(1-Thio-β-D-galactopyranosyl)cyclohex-2-yl]-L-histidine H2

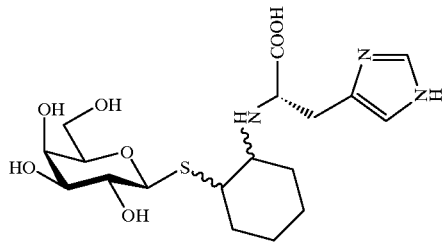

The title compound was prepared according to procedures D, H and N above using 2-chlorocyclohexanone as the electrophile and L-histidine methyl ester as the amino acid ester. Mass spectra data was as follows: M (calcd.): 431.50; M (found): 433.6 (M+H$^+$).

Example 41

Synthesis of N$^\alpha$-[1-(1-Thio-β-D-galactopyranosyl)cyclohept-3-yl]-L-histidine H5

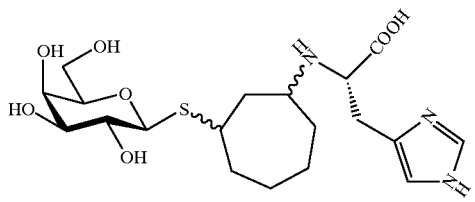

The title compound was prepared according to procedures D, H and N above using cyclohept-2-en-1-one as the electrophile and L-histidine methyl ester as the amino acid ester. Mass spectra data was as follows: M (calcd.): 445.54; M (found): 448.0 (M+H$^+$).

Example 42

Synthesis of N$^\alpha$-[1-(1-Thio-β-D-galactopyranosyl)-6,6-dimethylcyclohex-3-yl]-L-histidine H9

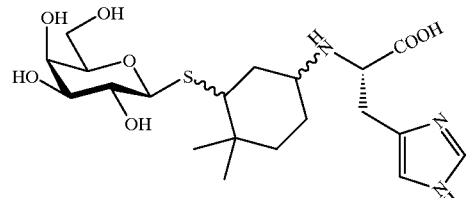

The title compound was prepared according to procedures D, H and N above using 4,4-dimethylcyclohex-2-en-1-one as the electrophile and L-histidine methyl ester as the amino acid ester. Mass spectra data was as follows: M (calcd.): 459.56; M (found): 462.2 (M+H$^+$).

Example 43

Synthesis of N$^\alpha$-[1-(1-Thio-β-D-galactopyranosyl)cyclohex-3-yl]-L-histidine H10

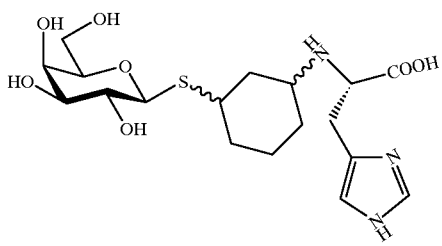

The title compound was prepared according to procedures D, H and N above using cyclohex-2en-1-one as the electrophile and L-histidine methyl ester as the amino acid ester. Mass spectra data was as follows: M (calcd.): 431.51; M (found): 433.2 (M+H$^+$).

Example 44

Synthesis of N$^\alpha$-[1-(1-Thio-β-D-galactopyranosyl)cyclohex-2-yl]-L-tryptophan I2

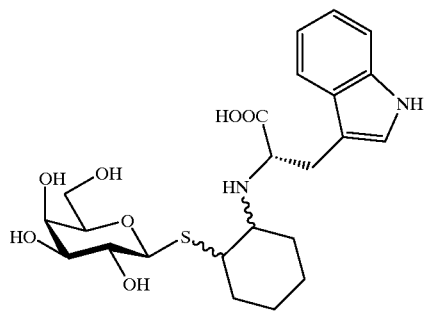

The title compound was prepared according to procedures D, H and N above using 2-chlorocyclohexanone as the electrophile and L-tryptophan methyl ester as the amino acid ester. Mass spectra data was as follows: M (calcd.): 480.59; M (found): 481.9 (M+H$^+$), 505.3 (M+Na$^+$).

Example 45

Synthesis of N$^\alpha$-[1-(1-Thio-β-D-galactopyranosyl)cyclohept-3-yl]-L-tryptophan I5

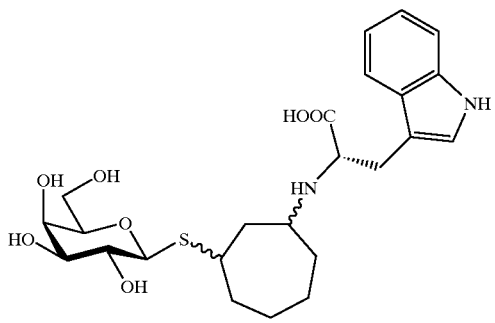

The title compound was prepared according to procedures D, H and N above using cyclohept-2-en-1-one as the electrophile and L-tryptophan methyl ester as the amino acid ester. Mass spectra data was as follows: M (calcd.): 480.58; M (found): 495.9 (M+H$^+$).

Example 46

Synthesis of N$^\alpha$-[1-(1-Thio-β-D-galactopyranosyl))-6,6-dimethylcyclohept-3-yl]-L-tryptophan I9

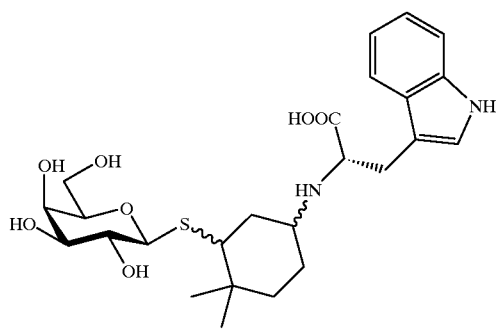

The title compound was prepared according to procedures D, H and N above using 4,4-dimethylcyclohex-2-en-1-one as the electrophile and L-tryptophan methyl ester as the amino acid ester. Mass spectra data was as follows: M (calcd.): 508.63; M (found): 512.1 (M+H$^+$).

Example 47

Synthesis of N$^\alpha$-[1-(1-Thio-β-D-galactopyranosyl)cyclohept-3-yl]-L-tryptophan I10

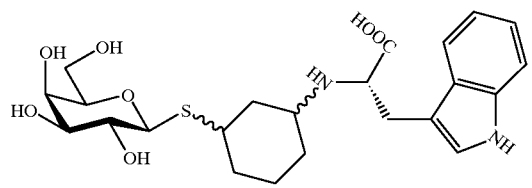

The title compound was prepared according to procedures D, H and N above using cyclohex-2en-I1-one as the electrophile and L-tryptophan methyl ester as the amino acid ester. Mass spectra data was as follows: M (calcd.): 480.59; M (found): 483.9 (M+H$^+$).

Example 48

Synthesis of N$^\alpha$-[1-(1-Thio-β-D-galactopyranosyl)cyclohex-2-yl]-L-arginine J2

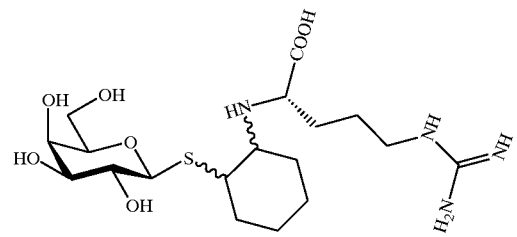

The title compound was prepared according to procedures D, H and O above using 2-chlorocyclopentanone as the electrophile and L-arginine methyl ester as the amino acid ester. Mass spectra data was as follows: M (calcd.): 450.56; M (found): 453.5 (M+H⁺).

Example 49

Synthesis of N^α-[1-(1-Thio-β-D-galactopyranosyl) cyclohept-3-yl]-L-arginine J5

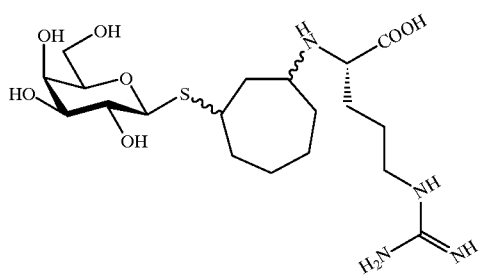

The title compound was prepared according to procedures D, H and O above using cyclohept-2en-1-one as the electrophile and L-arginine methyl ester as the amino acid ester. Mass spectra data was as follows: M (calcd.): 464.58; M (found): 467.1 (M+H⁺).

Example 50

Synthesis of N^α-[1-(1-Thio-β-D-galactopyranosyl) cyclopent-3-yl]-L-arginine J7

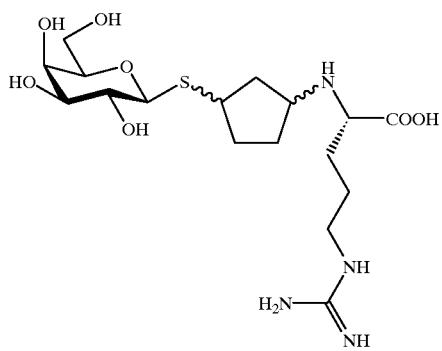

The title compound was prepared according to procedures D, H and O above using cyclopent-2-en-1-one as the electrophile and L-arginine methyl ester as the amino acid ester. Mass spectra data was as follows: M (calcd.): 436.53; M (found): n.a. Selected nmr data was as follows: 1H-nmr (CD₃OD): δ 4.18, 4.17, 4.16, and 4.15 (4 d, J 10 Hz), 3.90 (br d, J 3.6 Hz), 2.37, 2.04, and 1.53 (3 m).

Example 51

Synthesis of 4,4-Dimethyl-3-hydroxycyclohexyl 1-Thio-β-D-galactopyranoside A8

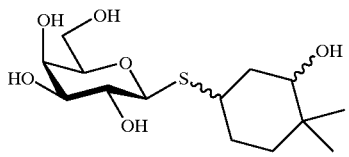

The title compound was prepared according to procedures D, E and I above using 6,6-dimethylcyclohex-2-en-1-one as the electrophile.

Example 52

Synthesis of 3-Amino-4,4-dimethylcyclohexyl 1-Thio-β-D-galactopyranoside B8

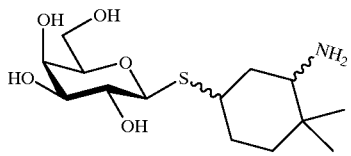

The title compound was prepared according to procedure D, F and J above using 6,6-dimethylcyclohex-2-en-1-one as the electrophile.

Example 53

Synthesis of 3-Acetamido-4,4-dimethylcyclohexyl 1-Thio-β-D-galactopyranoside C8

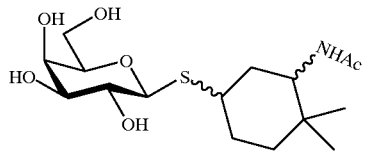

The title compound was prepared according to procedures D, F, J and K above using 6,6-dimethylcyclohex-2-en-1-one as the electrophile.

Example 54

Synthesis of N^α-[1-(1-Thio-β-D-galactopyranosyl)-4,4-dimethylcyclohex-3-yl]-glycine E8

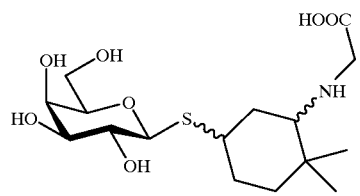

The title compound was prepared according to procedures D, H and M above using 6,6-dimethylcyclohex-2-en-1-one as the electrophile and glycine tert-butyl ester as the amino acid ester.

Example 55

Synthesis of N$^\beta$-[1-(1-Thio-β-D-galactopyranosyl)-4,4-methylcyclohex-3-yl]-β-alanine F8

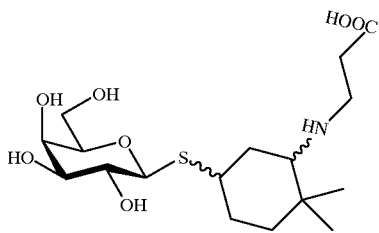

The title compound was prepared according to procedures D, H and M above using 6,6-dimethylcyclohex-2-en-1-one as the electrophile and β-alanine tert-butyl ester as the amino acid ester.

Example 56

Inhibition of Heat-Labile Enterotoxin Binding to $G_{D1b}$

The 1-thiogalactose derivatives prepared above were tested for their ability to inhibit the binding of heat-labile enterotoxin from *E. coli* to ganglioside $G_{D1b}$. This bioassay was conducted using the procedure described by A.-M. Svennerholm[7] except that ganglioside $G_{D1b}$ was used instead of ganglioside $G_{M1}$. The results of this assay evidenced that each of the compounds of Examples 1, 3, 5, 8–18, 21, 22, 24–26, 29–33, 35, 37–39, 44, 45, 50–55 inhibited binding of heat-labile enterotoxin to ganglioside $G_{D1b}$ by at least 20%.

From the foregoing description, various modifications and changes in the composition and method will occur to those skilled in the art. All such modifications coming within the scope of the appended claims are intended to be included therein.

What is claimed is:

1. A compound of the formula:

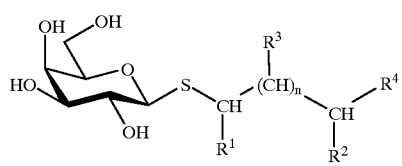

I wherein
  $R^1$ is selected from the group consisting of:
    hydrogen,
    alkyl,
    alkyl substituted with from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy and thioheteroaryloxy,
    alkenyl,
    alkaryl,
    alkoxyalkyl,
    aryl,
    cycloalkyl,
    cycloalkenyl,
    heteroaryl,
    heterocyclic and
    thioalkoxyalkyl;
  $R^2$ is selected from the group consisting of:
    hydrogen,
    alkyl,
    alkyl substituted with from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy and thioheteroaryloxy,
    alkenyl,
    alkaryl,
    alkoxyalkyl,
    aryl,
    cycloalkyl,
    cycloalkenyl,
    heteroaryl,
    heterocyclic and
    thioalkoxyalkyl;
  $R^3$ is selected from the group consisting of:
    hydrogen,
    alkyl,
    alkyl substituted with from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy and thioheteroaryloxy,
    alkenyl,
    alkaryl,
    alkoxyalkyl,
    aryl,
    cycloalkyl,
    cycloalkenyl,
    heteroaryl,
    heterocyclic and
    thioalkoxyalkyl;
  wherein $R^1$ and $R^2$ or $R^1$ and $R^3$ or $R^2$ and $R^3$ can be joined, together with the carbon atoms to which $R^1$ and/or $R^2$ and/or $R^3$ are attached, to form a cycloalkyl ring, a cycloalkenyl ring, or a heterocyclic ring;
  $R^4$ is selected from the group consisting of —XR$^5$, —XC(O)R$^6$, —XC(O)X'R$^7$ and —C(O)XR$^8$;
  wherein X and X' are each independently selected from the group consisting of oxygen, sulfur and —NR$^9$—, wherein $R^9$ is selected from the group consisting of hydrogen and allyl;
  $R^5$ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is —NR$^9$—, then $R^9$ together with $R^5$ can form an amino acid;
  $R^6$ is selected from the group consisting of alkyl, alkenyl, alkaryl, alkoxyalkyl, aryl, cycloalkyl, cycloalkenyl, heteroaryl, heterocyclic and thioalkoxyalkyl;
  $R^7$ is selected from the group consisting of alkyl, alkenyl, alkaryl, alkoxyalkyl, aryl, cycloalkyl, cycloalkenyl, heteroaryl, heterocyclic and thioalkoxyalkyl;
  $R^8$ is selected from the group consisting of alkyl, alkenyl, alkaryl, alkoxyalkyl, aryl, cycloalkyl, cycloalkenyl, heteroaryl, heterocyclic and thioalkoxyalkyl; and n is an integer equal to 0 or 1;
with the provisos that:
when $R^1$ and $R^2$ are joined, together with the carbon atoms to which they are attached, to form a cyclohexyl ring, $R^4$ is —$XR^5$, X is oxygen and n is 0, then $R^5$ is not hydrogen;
when $R^1$ and $R^2$ are joined, together with the carbon atoms to which they are attached, to form a cyclohexyl ring, $R^4$ is —$XC(O)R^6$, X is —NH— and n is 0, then $R^6$ is not 2-carboxyphenyl;
when $R^1$ and $R^2$ are joined, together with the carbon atoms to which they are attached, to form a cyclohexyl ring, $R^4$ is —$XR^5$, X is —$NR^9$— and n is 0, then X and $R^5$ together do not form the amino acid L-leucine;
when $R^1$ and $R^2$ are joined, together with the carbon atoms to which $R^1$, $R^2$ and $R^3$ are attached, to form a cyclopentyl or cycloheptyl ring, $R^3$ is hydrogen, $R^4$ is —$XR^5$, X is oxygen and n is 1, then $R^5$ is not hydrogen;
when $R^1$ and $R^2$ are joined, together with the carbon atoms to which $R^1$, $R^2$ and $R^3$ are attached, to form a cyclohexyl ring, $R^3$ is hydrogen, $R^4$ is —$C(O)R^6$, X is —NH— and n is 1, then $R^6$ is not methyl, and
when $R^1$ and $R^2$ are each hydrogen, $R^4$ is —$XR^5$, X is oxygen and n is 0, then $R^5$ is not hydrogen or phenyl; and when $R^1$ and $R^2$ are each hydrogen, $R^4$ is —$XR^5$, X is —NH— and n is 0, then $R^5$ is not phenyl.

2. A compound of claim 1 wherein, when n is 0, $R^1$ and $R^2$ are joined, together with the carbon to which they are attached, to form a cyclopentane or cyclohexane ring.

3. A compound of claim 1 wherein, when n is 1, $R^1$ and $R^2$ are joined, together with the carbon atoms to which $R^1$, $R^2$ and $R^3$ are attached, to form a cyclopentane, cyclohexane, or cycloheptane ring.

4. A compound of claim 1 wherein, when n is 1, $R^2$ and $R^3$ are joined, together with the carbon atoms to which they are attached, to form a bicyclo[2.2.1]heptane ring.

5. A compound of claim 1 wherein $R^4$ is —$XR^1$ where X and $R^5$ form an amino group, a hydroxy group or an amino acid selected from the group consisting of glycine, β-alanine, leucine and tryptophan.

6. A compound of claim 1 wherein $R^4$ is —$XC(O)R^6$ where X is —NH— and $R^6$ is methyl or (2-carboxyphenyl).

7. A compound selected from the group consisting of:
2-hydroxycyclopentyl 1-thio-β-D-galactopyranoside,
(2-hydroxybicyclo[2.2.1]cycloheptyl)methyl 1-thio-β-D-galactopyranoside,
5,5-dimethyl-3-hydroxycyclopentyl 1-thio-β-D-galactopyranoside,
6,6-dimethyl-3-hydroxycyclohexyl 1-thio-β-D-galactopyranoside,
3-hydroxycyclohexyl 1-thio-β-D-galactopyranoside,
2-aminocyclopentyl 1-thio-β-D-galactopyranoside,
2-aminocyclohexyl 1-thio-β-D-galactopyranoside,
(2-aminobicyclo[2.2.1]cycloheptyl)methyl 1-thio-β-D-galactopyranoside,
3-aminocycloheptyl 1-thio-β-D-galactopyranoside,
5,5-dimethyl-3-aminocyclopentyl 1-thio-β-D-galactopyranoside,
3-aminocyclopentyl 1-thio-β-D-galactopyranoside,
3-aminocyclohexyl 1-thio-β-D-galactopyranoside,
2-acetamidocyclohexyl 1-thio-β-D-galactopyranoside,
3-acetamidocycloheptyl 1-thio-β-D-galactopyranoside,
3-acetamidocyclopentyl 1-thio-β-D-galactopyranoside,
(2-(carboxybenzamido)bicyclo[2.2.1]cycloheptyl)methyl 1-thio-β-D-galactopyranoside,
3-(2-carboxybenzamido)cycloheptyl 1-thio-β-D-galactopyranoside,
6,6-dimethyl-3-(2-carboxybenzamido)cyclohexyl 1-thio-β-D-galactopyranoside,
$N^\alpha$-[1-(1-Thio-β-D-galactopyranosyl)cyclohex-2-yl]-glycine,
$N^\alpha$-[1-(1-Thio-β-D-galactopyranosyl)methyl)bicyclo[2.2.1]hept-2-yl]-glycine,
$N^\alpha$-[1-(1-Thio-β-D-galactopyranosyl)cyclohept-3-yl]-glycine,
$N^\alpha$-[1-(1-Thio-β-D-galactopyranosyl)-6,6-dimethylcyclohex-3-yl]-glycine,
$N^\alpha$-[1-(1-Thio-β-D-galactopyranosyl)cyclohex-3-yl]-glycine,
$N^\beta$-[1-(1-Thio-β-D-galactopyranosyl)cyclopent-2-yl]-β-alanine,
$N^\beta$-[1-(1-Thio-β-D-galactopyranosyl)cyclohept-3-yl]-β-alanine,
$N^\beta$-[1-(1-Thio-β-D-galactopyranosyl)cyclopent-3-yl]-β-alanine,
$N^\beta$-[1-(1-Thio-β-D-galactopyranosyl)-6,6-methylcyclohex-3-yl]-β-alanine,
$N^\beta$-[1-(1-Thio-β-D-galactopyranosyl)cyclohex-3-yl]-β-alanine,
$N^\alpha$-[1-(1-Thio-β-D-galactopyranosyl)cyclohept-3-yl]-L-leucine,
$N^\alpha$-[1-(1-Thio-β-D-galactopyranosyl)-6,6-dimethylcyclohex-3-yl]-L-leucine,
$N^\alpha$-[1-(1-Thio-β-D-galactopyranosyl)cyclohex-3-yl]-L-leucine,
$N^\alpha$-[1-(1-Thio-β-D-galactopyranosyl)cyclohex-2-yl]-L-histidine,
$N^\alpha$-[1-(1-Thio-β-D-galactopyranosyl)cyclohept-3-yl]-L-histidine,
$N^\alpha$-[1-(1-Thio-β-D-galactopyranosyl)-6,6-dimethylcyclohex-3-yl]-L-histidine,
$N^\alpha$-[1-(1-Thio-β-D-galactopyranosyl)cyclohex-3-yl]-L-histidine,
$N^\alpha$-[1-(1-Thio-β-D-galactopyranosyl)cyclohex-2-yl]-L-tryptophan,
$N^\alpha$-[1-(1-Thio-β-D-galactopyranosyl)cyclohept-3-yl]-L-tryptophan,
$N^\alpha$-[1-(1-Thio-β-D-galactopyranosyl)-6,6-dimethylcyclohept-3-yl]-L-tryptophan,
$N^\alpha$-[1-(1-Thio-β-D-galactopyranosyl)cyclohept-3-yl]-L-tryptophan,
$N^\alpha$-[1-(1-Thio-β-D-galactopyranosyl)cyclohex-2-yl]-L-arginine,
$N^\alpha$-[1-(1-Thio-β-D-galactopyranosyl)cyclohept-3-yl]-L-arginine,
$N^\alpha$-[1-(1-Thio-β-D-galactopyranosyl)cyclopent-3-yl]-L-arginine,
$N^\alpha$-[1-(1-Thio-β-D-galactopyranosyl)cyclopent-2-yl]-glycine,
$N^\beta$-[1-(1-Thio-β-D-galactopyranosyl)cyclohex-2-yl]-β-alanine,
4,4-dimethyl-3-hydroxycyclohexyl 1-thio-β-D-galactopyranoside,
3-amino-4,4-dimethylcyclohexyl 1-thio-β-D-galactopyranoside, 3-acetamido-4,4-dimethylcyclohexyl 1-thio-β-D-galactopyranoside, N$^\alpha$-[1-(1-Thio-β-D-galactopyranosyl)-4,4-dimethylcyclohex-3-yl]-glycine, and N$^\beta$-[1-(1-Thio-β-D-galactopyranosyl)-4,4-methylcyclohex-3-yl]-β-alanine.

8. A pharmaceutical composition comprising from 1 to 99 weight percent of a pharmaceutically acceptable excipient and from 1 to 99 weight percent of a compound of the formula:

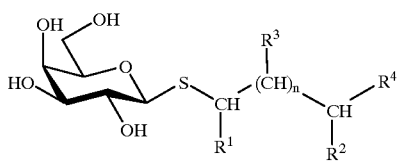

I wherein
  $R^1$ is selected from the group consisting of:
    hydrogen,
    alkyl,
    alkyl substituted with from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy and thioheteroaryloxy,
    alkenyl,
    alkaryl,
    alkoxyalkyl,
    aryl,
    cycloalkyl,
    cycloalkenyl,
    heteroaryl,
    heterocyclic and
    thioalkoxyalkyl;
  $R^2$ is selected from the group consisting of:
    hydrogen,
    alkyl,
    alkyl substituted with from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy and thioheteroaryloxy,
    alkenyl,
    alkaryl,
    alkoxyalkyl,
    aryl,
    cycloalkyl,
    cycloalkenyl,
    heteroaryl,
    heterocyclic and
    thioalkoxyalkyl;
  $R^3$ is selected from the group consisting of:
    hydrogen,
    alkyl,
    alkyl substituted with from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy and thioheteroaryloxy,
    alkenyl,
    alkaryl,
    alkoxyalkyl,
    aryl,
    cycloalkyl,
    cycloalkenyl,
    heteroaryl,
    heterocyclic and
    thioalkoxyalkyl;
  wherein $R^1$ and $R^2$ or $R^1$ and $R^3$ or $R^2$ and $R^3$ can be joined, together with the carbon atoms to which $R^1$ and/or $R^2$ and/or $R^3$ are attached, to form a cycloalkyl ring, a cycloalkenyl ring, or a heterocyclic ring;
  $R^5$ is selected from the group consisting of —$XR^5$, —$XC(O)R^6$, —$XC(O)X'R^7$ and —$C(O)XR^8$;
  wherein X and X' are each independently selected from the group consisting of oxygen, sulfur and —$NR^9$—, wherein $R^9$ is selected from the group consisting of hydrogen and alkyl;
  $R^5$ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is —$NR^9$—, then $R^9$ together with $R^5$ can form an amino acid;
  $R^6$ is selected from the group consisting of alkyl, alkenyl, alkaryl, alkoxyalkyl, aryl, cycloalkyl, cycloalkenyl, heteroaryl, heterocyclic and thioalkoxyalkyl;
  $R^7$ is selected from the group consisting of alkyl, alkenyl, alkaryl, alkoxyalkyl, aryl, cycloalkyl, cycloalkenyl, heteroaryl, heterocyclic and thioalkoxyalkyl;
  $R^8$ is selected from the group consisting of alkyl, alkenyl, alkaryl, alkoxyalkyl, aryl, cycloalkyl, cycloalkenyl, heteroaryl, heterocyclic and thioalkoxyalkyl; and
  n is an integer equal to 0 or 1;
  with the provisos that:
    when $R^1$ and $R^2$ are joined, together with the carbon atoms to which they are attached, to form a cyclohexyl ring, $R^1$ is —$XR^5$, X is oxygen and n is 0, then $R^5$ is not hydrogen;
    when $R^1$ and $R^2$ are joined, together with the carbon atoms to which they are attached, to form a cyclohexyl ring, $R^4$ is —$XC(O)R^6$, X is —NH— and n is 0, then $R^6$ is not 2-carboxyphenyl;
    when $R^1$ and $R^2$ are joined, together with the carbon atoms to which they are attached, to form a cyclohexyl ring, $R^4$ is —$XR^1$, X is —$NR^9$— and n is 0, then X and $R^5$ together do not form the amino acid L-leucine;
    when $R^1$ and $R^2$ are joined, together with the carbon atoms to which $R^1$, $R^2$ and $R^3$ are attached, to form a cyclopentyl or cycloheptyl ring, $R^3$ is hydrogen, $R^4$ is —$XR^5$, X is oxygen and n is 1, then $R^5$ is not hydrogen;
    when $R^1$ and $R^2$ are joined, together with the carbon atoms to which $R^1$, $R^2$ and $R^3$ are attached, to form a cyclohexyl ring, $R^3$ is hydrogen, $R^4$ is —$C(O)R^6$, X is —NH— and n is 1, then $R^6$ is not methyl, and
    when $R^1$ and $R^2$ are each hydrogen $R^4$ is —$XR^5$, X is oxygen and n is 0, then $R^5$ is not hydrogen or phenyl; and when $R^1$ and $R^2$ are each hydrogen, $R^4$ is —$XR^5$, X is —NH— and n is 0, then $R^5$ is not phenyl.

9. A pharmaceutical composition comprising from 1 to 99 weight percent of a pharmaceutically acceptable excipient and from 1 to 99 weight percent of a compound selected from the group consisting of:

2-hydroxycyclopentyl 1-thio-β-D-galactopyranoside,
(2-hydroxybicyclo[2.2.1]cycloheptyl)methyl 1-thio-β-D-galactopyranoside,
5,5-dimethyl-3-hydroxycyclopentyl 1-thio-β-D-galactopyranoside,
6,6-dimethyl-3-hydroxycyclohexyl 1-thio-β-D-galactopyranoside,
3-hydroxycyclohexyl 1-thio-β-D-galactopyranoside,
2-aminocyclopentyl 1-thio-β-D-galactopyranoside,
2-aminocyclohexyl 1-thio-β-D-galactopyranoside,
(2-aminobicyclo[2.2.1]cycloheptyl)methyl 1-thio-β-D-galactopyranoside,
3-aminocycloheptyl 1-thio-β-D-galactopyranoside,
5,5-dimethyl-3-aminocyclopentyl 1-thio-β-D-galactopyranoside,
3-aminocyclopentyl 1-thio-β-D-galactopyranoside,
3-aminocyclohexyl 1-thio-β-D-galactopyranoside,
2-acetamidocyclohexyl 1-thio-β-D-galactopyranoside,
3-acetamidocycloheptyl 1-thio-β-D-galactopyranoside,
3-acetamidocyclopentyl 1-thio-β-D-galactopyranoside,
(2-(carboxybenzamido)bicyclo[2.2.1]cycloheptyl)methyl 1-thio-β-D-galactopyranoside,
3-(2-carboxybenzamido)cycloheptyl 1-thio-β-D-galactopyranoside,
6,6-dimethyl-3-(2-carboxybenzamido)cyclohexyl 1-thio-β-D-galactopyranoside,
$N^\alpha$-[1-(1-Thio-β-D-galactopyranosyl)cyclohex-2-yl]-glycine,
$N^\alpha$-[1-(1-Thio-β-D-galactopyranosyl)methyl)bicyclo[2.2.1]hept-2-yl]-glycine,
$N^\alpha$-[1-(1-Thio-β-D-galactopyranosyl)cyclohept-3-yl]-glycine,
$N^\alpha$-[1-(1-Thio-β-D-galactopyranosyl)-6,6-dimethylcyclohex-3-yl]-glycine,
$N^\alpha$-[1-(1-Thio-β-D-galactopyranosyl)cyclohex-3-yl]-glycine,
$N^\alpha$-[1-(1-Thio-β-D-galactopyranosyl)cyclopent-2-yl]-β-alanine,
$N^\alpha$-[1-(1-Thio-β-D-galactopyranosyl)cyclohept-3-yl]-β-alanine,
$N^\alpha$-[1-(1-Thio-β-D-galactopyranosyl)cyclopent-3-yl]-β-alanine,
$N^\alpha$-[1-(1-Thio-β-D-galactopyranosyl)-6,6-methylcyclohex-3-yl]-β-alanine,
$N^\alpha$-[1-(1-Thio-β-D-galactopyranosyl)cyclohex-3-yl]-β-alanine,
$N^\alpha$-[1-(1-Thio-β-D-galactopyranosyl)cyclohept-3-yl]-L-leucine,
$N^\alpha$-[1-(1-Thio-β-D-galactopyranosyl)-6,6-dimethylcyclohex-3-yl]-L-leucine,
$N^\alpha$-[1-(1-Thio-β-D-galactopyranosyl)cyclohex-3-yl]-L-leucine,
$N^\alpha$-[1-(1-Thio-β-D-galactopyranosyl)cyclohex-2-yl]-L-histidine,
$N^\alpha$-[1-(1-Thio-β-D-galactopyranosyl)cyclohept-3-yl]-L-histidine,
$N^\alpha$-[1-(1-Thio-β-D-galactopyranosyl)-6,6-dimethylcyclohex-3-yl]-L-histidine,
$N^\alpha$-[1-(1-Thio-β-D-galactopyranosyl)cyclohex-3-yl]-L-histidine,
$N^\alpha$-[1-(1-Thio-β-D-galactopyranosyl)cyclohex-2-yl]-L-tryptophan,
$N^\alpha$-[1-(1-Thio-β-D-galactopyranosyl)cyclohept-3-yl]-L-tryptophan,
$N^\alpha$-[1-(1-Thio-β-D-galactopyranosyl)-6,6-dimethylcyclohept-3-yl]-L-tryptophan,
$N^\alpha$-[1-(1-Thio-β-D-galactopyranosyl)cyclohept-3-yl]-L-tryptophan,
$N^\alpha$-[1-(1-Thio-β-D-galactopyranosyl)cyclohex-2-yl]-L-arginine,
$N^\alpha$-[1-(1-Thio-β-D-galactopyranosyl)cyclohept-3-yl]-L-arginine,
$N^\alpha$-[1-(1-Thio-β-D-galactopyranosyl)cyclopent-3-yl]-L-arginine,
$N^\alpha$-[1-(1-Thio-β-D-galactopyranosyl)cyclopent-2-yl]-glycine,
$N^\beta$-[1-(1-Thio-β-D-galactopyranosyl)cyclohex-2-yl]-β-alanine,
4,4-dimethyl-3-hydroxycyclohexyl 1-thio-β-D-galactopyranoside,
3-amino-4,4-dimethylcyclohexyl 1-thio-β-D-galactopyranoside,
3-acetamido-4,4-dimethylcyclohexyl 1-thio-β-D-galactopyranoside,
$N^\alpha$-[1-(1-Thio-β-D-galactopyranosyl)-4,4-dimethylcyclohex-3-yl]-glycine, and
$N^\beta$-[1-(1-Thio-β-D-galactopyranosyl)-4,4-methylcyclohex-3-yl]-β-alanine.

10. A method to inhibit the conditions associated with binding of heat labile toxin (LT) and/or chlorea toxin (CT) to a cell surface receptor in a mammal in need of such inhibition which method comprises administering to said mammal an effective amount of a pharmaceutical composition of claim 8.

11. A method to inhibit the conditions associated with binding of heat labile toxin (LT) and/or chlorea toxin (CT) to a cell surface receptor in a mammal in need of such inhibition which method comprises administering to said mammal an effective amount of a pharmaceutical composition of claim 9.

12. A method to inhibit the conditions associated with binding of *Vibrio cholerae* or enterotoxigenic strains of *Escherichia coli* to cell surface receptors in a mammal in need of such inhibition which method comprises administering to said mammal an effective amount of a pharmaceutical composition of claim 8.

13. A method to inhibit the conditions associated with binding of *Vibrio cholerae* or enterotoxigenic strains of *Escherichia coli* to cell surface receptors in a mammal in need of such inhibition which method comprises administering to said mammal an effective amount of a pharmaceutical composition of claim 9.

* * * * *